(12) United States Patent
Mann

(10) Patent No.: US 12,215,306 B2
(45) Date of Patent: Feb. 4, 2025

(54) LAGOON COVER

(71) Applicant: BENNAMANN SERVICES LTD, Newquay (GB)

(72) Inventor: Christopher Mark Mann, St. Mawgan (GB)

(73) Assignee: BENNAMANN SERVICES LTD, Newquay (GB)

( * ) Notice: Subject to any disclaimer, the term of this patent is extended or adjusted under 35 U.S.C. 154(b) by 0 days.

(21) Appl. No.: 18/277,038

(22) PCT Filed: Feb. 14, 2022

(86) PCT No.: PCT/IB2022/051297
§ 371 (c)(1),
(2) Date: Aug. 11, 2023

(87) PCT Pub. No.: WO2022/172243
PCT Pub. Date: Aug. 18, 2022

(65) Prior Publication Data
US 2024/0034972 A1    Feb. 1, 2024

Related U.S. Application Data

(60) Provisional application No. 63/149,573, filed on Feb. 15, 2021.

(51) Int. Cl.
*B65G 5/00* (2006.01)
*C12M 1/00* (2006.01)
(Continued)

(52) U.S. Cl.
CPC ............ *C12M 23/38* (2013.01); *C12M 21/04* (2013.01); *C12M 23/18* (2013.01); *C12M 23/26* (2013.01);
(Continued)

(58) Field of Classification Search
CPC ... B65G 5/00; F17C 1/007; E04H 7/02; Y02E 50/30; Y02E 50/10; Y02C 20/40; Y02C 20/20
See application file for complete search history.

(56) References Cited

U.S. PATENT DOCUMENTS

| | | | | |
|---|---|---|---|---|
| 3,769,763 A | * | 11/1973 | Kwake | E04H 15/22 428/167 |
| 5,246,308 A | * | 9/1993 | Brothers | E04H 4/142 405/53 |
| 5,346,329 A | * | 9/1994 | Goans | E02B 15/0864 405/63 |

FOREIGN PATENT DOCUMENTS

| | | |
|---|---|---|
| CN | 203582854 U | 5/2014 |
| CN | 204385190 U | 6/2015 |

(Continued)

OTHER PUBLICATIONS https://www.thefreedictionary.com/fuzes; 2024.*

(Continued)

*Primary Examiner* — Sean D Andrish
(74) *Attorney, Agent, or Firm* — Rothwell, Figg, Ernst & Manbeck, P.C.

(57) ABSTRACT

A cover for a lagoon is provided. The cover includes an expandable membrane; a plurality of stretchable members coupled to the expandable membrane and configured to compress the expandable membrane; and a plurality of restraining members coupled to the expandable membrane and configured to limit expansion of the expandable membrane.

23 Claims, 26 Drawing Sheets

(51) Int. Cl.
  *C12M 1/107*   (2006.01)
  *E04H 7/02*    (2006.01)
  *F17C 1/00*    (2006.01)
(52) U.S. Cl.
  CPC ............... *B65G 5/00* (2013.01); *E04H 7/02* (2013.01); *F17C 1/007* (2013.01)

(56) References Cited

FOREIGN PATENT DOCUMENTS

| | | | |
|---|---|---|---|
| CN | 105199943 | A | 12/2015 |
| CN | 206736234 | U | 12/2017 |
| CN | 109943477 | A | 6/2019 |
| EP | 1801037 | A1 | 6/2007 |
| EP | 3321350 | A1 | 5/2018 |
| JP | 2011050917 | * | 3/2011 |
| WO | 2020225794 | A1 | 11/2020 |

OTHER PUBLICATIONS

First Office Action issued in CN2022800149451 dated Nov. 27, 2023 (16 pages).
International Search Report and Written Opinion dated May 17, 2022, issued in International Patent Application No. PCT/IB2022/051297 (12 pages).
International Preliminary Examination Report dated Mar. 7, 2023, issued in International Patent Application No. PCT/IB2022/051297 (9 pages).

* cited by examiner

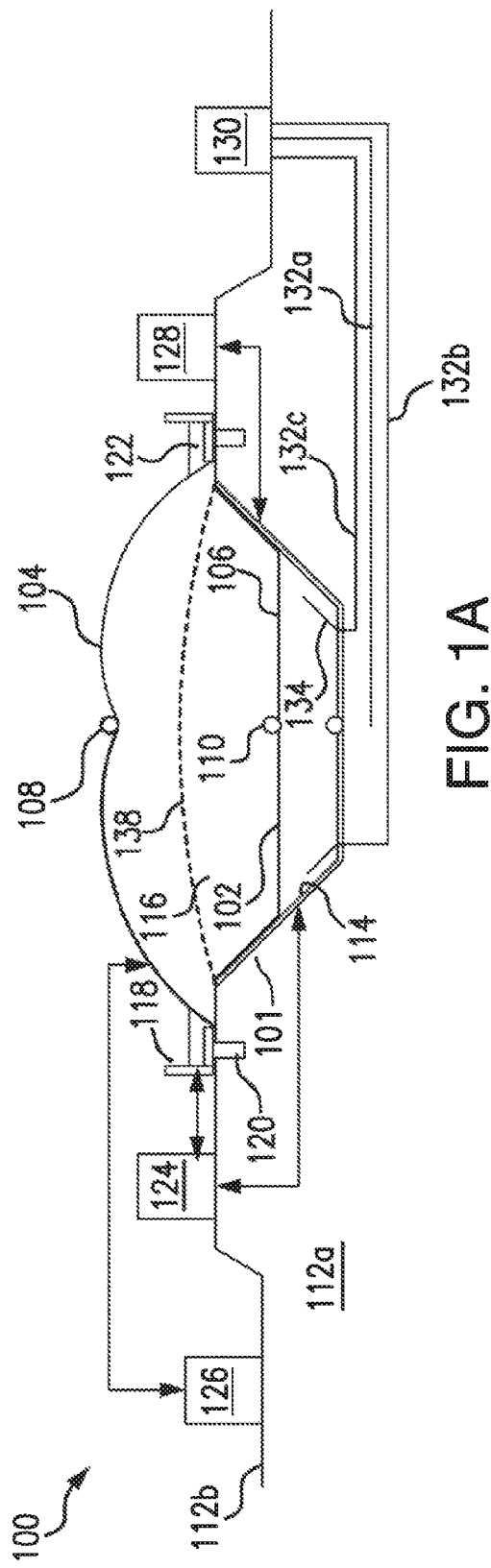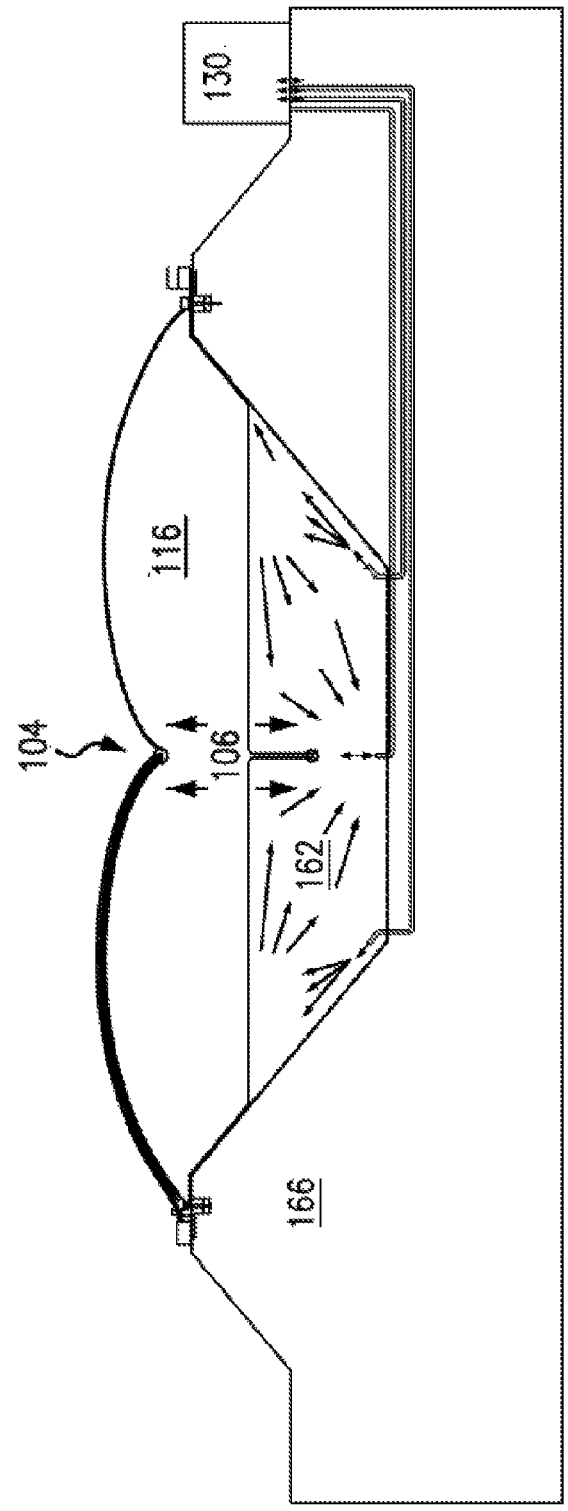

LAGOON COVER

CROSS REFERENCE TO RELATED APPLICATIONS

This application is a 35 U.S.C. § 371 National Stage of International Patent Application No. PCT/IB2022/051297, filed 2022 Feb. 14, which claims priority to U.S. Provisional Patent Application No. 63/149,573, filed on 2021 Feb. 15, the disclosures of which are incorporated herein in their entirety by reference.

FIELD OF THE DISCLOSURE

This disclosure relates generally to anaerobic digestion and related processing of gaseous materials, and in particular, a covered anaerobic digest system and the installation or operation thereof, and lagoon covers.

BACKGROUND

Anaerobic Digestion

Anaerobic digestion is a process that can be used to convert a wide range of biomass materials into useable gas, such as a gas comprising mostly methane and carbon dioxide ($CO_2$). Carbon dioxide can be used for a variety of purposes such as food and industrial processing. Methane, which may be more valuable than carbon dioxide, can be used as a direct replacement for fossil fuels such as oil and natural gas. When methane is generated from anaerobic digestion from organic matter (i.e., biomass), it is often referred to as biomethane.

Biomethane can be used as a fuel (e.g., for combustion engines or fuel cells) to provide power and heat. When biomethane is burnt, the exhaust typically comprises only carbon dioxide and water. In principle, the quantity of carbon dioxide released equals the amount that would have been released had the biomass had been allowed to aerobically decompose naturally; therefore, methane produced in this way is effectively considered a zero-carbon fuel. The use of anaerobic digestion of biomass to produce methane is therefore seen as an effective way to reduce the level of carbon dioxide in the atmosphere and help to mitigate climate change. Patent Application PCT/IB2020/054392, titled "Anaerobic Digester and Mobile Biogas Processing Plant," describes an anaerobic digester and certain gas processing devices and methods.

Because anaerobic digestion systems are often outdoors or otherwise exposed to natural elements (e.g., rain and snow), operation and monitoring of such systems may be difficult. Accordingly, there is a need for improved anaerobic digestion systems and methods, as well as associated gas processing.

Lagoon Cover

Anaerobic digestion is a process that can be used to convert a wide range of biomass materials into mostly methane and carbon dioxide gases. Carbon dioxide ($CO_2$) can be used for a variety of purposes such as food and industrial processing. Methane, which is typically more valuable than carbon dioxide, can be used as a direct replacement for fossil fuels such as oil and natural gas. When methane is generated from anaerobic digestion from organic matter (i.e., biomass), it is often referred to as biomethane.

Biomethane can be used as a fuel (e.g., for combustion engines or fuel cells) to provide power and heat. When biomethane is burnt, the exhaust comprises only carbon dioxide and water. In principle, the quantity of carbon dioxide released equals the amount that would have been released had the biomass had been allowed to aerobically decompose naturally; therefore, methane produced in this way is effectively considered a zero-carbon fuel. The use of anaerobic digestion of biomass to produce methane is therefore seen as an effective way to reduce the level of carbon dioxide in the atmosphere and help to mitigate climate change. An anaerobic digester is described in this disclosure, based on the disclosure of Patent Application U.S. 63/052, 190 and PCT/IB2021/056375, titled "Systems and Methods for Anaerobic Digestion".

Many types of biomass can be anaerobically digested. To achieve the most beneficial impact with respect to climate change, using anaerobic digestion to limit or eradicate "fugitive" emissions of methane (such as those that are currently created by the poor management of animal manures such as cow and pig slurry in open lagoons) may be most effective. The use of open-slurry lagoons in the agriculture sector results in very high levels of fugitive methane emissions. By sealing the slurry lagoon to prevent aerobic digestion, the methane can be contained. This practice can be advantageous for the purposes of limiting or eradicating "fugitive" emissions of methane, and in embodiments disclosed herein can also provide for considerable operational benefits. Such benefits may include:

Reduced nitrogen loss; this is because nitrogen is contained in the digestate (i.e., the material remaining after the anaerobic digestion of the biomass), which can in turn reduce the need for fertilizer when the digestate is spread back onto the land.

Reduced handling and management of slurry; this is because rain water is prevented from entering the covered lagoon, meaning that the digestate is more concentrated and there is less to spread.

Reduced risk of overspill; this is because rain water is prevented from entering the covered lagoon, and in turn minimizes the possibility of leakage of raw slurry into waterways (which may be illegal in many countries).

Reduced greenhouse gases; this is because biomass (such as waste or spoiled animal feed) is usually managed by composting aerobically and the energy held in it is lost as heat during this process, and may result in large quantities of methane and nitrous oxides, both powerful greenhouse gases. Such greenhouse gases are reduced, however, with the use of a sealed slurry lagoon, such as provided by embodiments disclosed herein.

Reduced energy demands; this is because anaerobically generated methane may be used as fuel for a generator, e.g. to generate electricity and heat that can be used on the farm, thereby offsetting its electricity and energy usage.

Where the installation cost of a covered slurry lagoon is kept low, the above benefits can provide a reasonable return on investment for small-to mid-sized farms as compared to an open slurry lagoon.

However, because anaerobic digestion systems are often outdoors or otherwise exposed to natural elements (e.g., rain and snow), operation and monitoring of such systems may be difficult. Accordingly, there remains a need for improved anaerobic digestion systems and methods.

SUMMARY

According to embodiments, a cover for a lagoon, and a system having a slurry lagoon and a cover for the slurry lagoon, are provided. These can have the benefits of:

controlling the amount of rainwater that enters the lagoon, thereby minimizing the necessary size of the lagoon for an application;

an edge sealing system that, when filled with water, permits the monitoring/detection of leaks in one or more seals;

an edge sealing system that directs rainwater into a storage system such that the collected rainwater can be used for a variety of farmyard tasks;

an edge sealing system that minimizes contact between the metallic parts of the covered lagoon and the biogas generated or stored therein, thus reducing the possibility of corrosion.

Other benefits include that the cover can capture, in some embodiments, 80-95% of fugitive methane, depending on lagoon shape and end conditions. Embodiments may also reduce rain loading, be retrofitted to any open slurry lagoon or pond (even grass banked), be cheap, stable in high winds, able to store significant volumes of cleaned biogas, may decrease slurry volumes for unloading and spreading, and utilize existing slurry handling. Embodiments may be long-lasting (e.g., for an XR5 geo-membrane or similar material, a 20-year lifetime can be expected), may be retrievable as a capital item making financing more readily available, and can get a farmer on the fugitive methane ladder, allowing the farmer to then invest in a full installation or slurry storage improvements.

Other features and characteristics of the subject matter of this disclosure, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures.

According to a first aspect, a cover for a lagoon is provided. The cover includes an expandable membrane. The cover includes a plurality of stretchable members coupled to the expandable membrane and configured to compress the expandable membrane. The cover includes a plurality of restraining members coupled to the expandable membrane and configured to limit expansion of the expandable membrane.

In some embodiments, the expandable membrane comprises a plurality of sections, and each of the plurality of stretchable members is at a location where two or more sections of the plurality of sections meet, and each of the plurality of restraining members is at a location where two or more sections of the plurality of sections meet. In some embodiments, the plurality of sections forms a matrix. In some embodiments, the cover further includes a skirt surrounding the outer perimeter of the expandable membrane. In some embodiments, the skirt comprises pressurized tubes. In some embodiments, the cover further includes a gas processing unit configured to process raw biogas from a gas outlet and to feed processed biogas into a gas inlet of the expandable membrane. In some embodiments, the plurality of stretchable members comprise elastic material within the expandable membrane and connected to a top surface and a bottom surface of an interior of the expandable membrane. In some embodiments, the plurality of stretchable members comprise a spring and pulley. In some embodiments, the spring comprises a clock spring.

In some embodiments, a top surface of an exterior of the expandable membrane has a sloping contour. In some embodiments, a top surface of an exterior of the expandable membrane has a concave shape. In some embodiments, an elasticity of the plurality of stretchable members is varied in order to define the top surface of the exterior of the expandable membrane. In some embodiments, the plurality of stretchable members comprise elastic material within the expandable membrane and connected to a top surface and a bottom surface of an interior of the expandable membrane. In some embodiments, the plurality of restraining members comprise rope within the expandable membrane and connected to a top surface and a bottom surface of an interior of the expandable membrane. In some embodiments, the rope of each restraining member is configured to be loose when the expandable membrane is empty and configured to be taut when the expandable membrane is full. In some embodiments, the cover further includes a water collecting area and a water outlet for allowing water on a top surface of an exterior of the expandable membrane to escape. In some embodiments, the expandable membrane comprises one or more of: an XR-5 geo-membrane, a Sattler Pro-Tex Polyplan composite, polypropylene, polyethylene, PEEK, PVC, PTFE, PPS, and ETFE. In some embodiments, the expandable membrane is expandable in a vertical direction such that an outer perimeter of the expandable membrane is resistant to expansion.

According to a second aspect, a system is provided. The system includes a slurry lagoon. The system includes a cover for the slurry lagoon. The cover includes an expandable membrane; a plurality of stretchable members coupled to the expandable membrane and configured to compress the expandable membrane; and a plurality of restraining members coupled to the expandable membrane and configured to limit expansion of the expandable membrane.

In some embodiments, the cover for the slurry lagoon is any one of the embodiments of the first aspect. In some embodiments, the system further includes a skirt surrounding the outer perimeter of the expandable membrane, wherein the skirt is within the slurry lagoon and configured to stay submerged in slurry in the slurry lagoon. In some embodiments, the skirt is weighted so that it remains submerged within the slurry lagoon. In some embodiments, there is a gap between an edge of the slurry lagoon and the skirt, and a liquid within the gap seals the slurry lagoon to prevent gas leakage. In some embodiments, the system further includes a water collecting area and a water outlet for allowing water on a top surface of an exterior of the expandable membrane to escape.

In some embodiments, the system further includes piping coupled to the water outlet so that escaping water can pass through the pipe by gravity. In some embodiments, the system further includes a pump and piping coupled to the water outlet so that escaping water can pass through the pipe by pumping. In some embodiments, the system further includes a gas processing unit configured to process raw biogas from a gas outlet coupled to the slurry lagoon and to feed processed biogas into a gas inlet of the expandable membrane. In some embodiments, the system further includes one or more of: (i) a gas processing system, (ii) a mobile processing system, (iii) a thermal management system, (iv) a water collection and re-use system, and (v) an energy recovery system, each as disclosed in the "Anaerobic Digestion" section of this disclosure.

According to a third aspect, a method for retrofitting an uncovered slurry lagoon with a cover is provided. The method includes installing a cover on an uncovered slurry lagoon. The cover is any one of the embodiments of the first aspect.

BRIEF DESCRIPTION OF THE DRAWINGS

The accompanying drawings, which are incorporated herein and form part of the specification, illustrate various embodiments of the subject matter of this disclosure. In the drawings, like reference numbers indicate identical or functionally similar elements.

Anaerobic Digestion

FIGS. 1A and 1B illustrate an anaerobic digestion system according to some embodiments.

Lagoon Cover

Figure 10A:
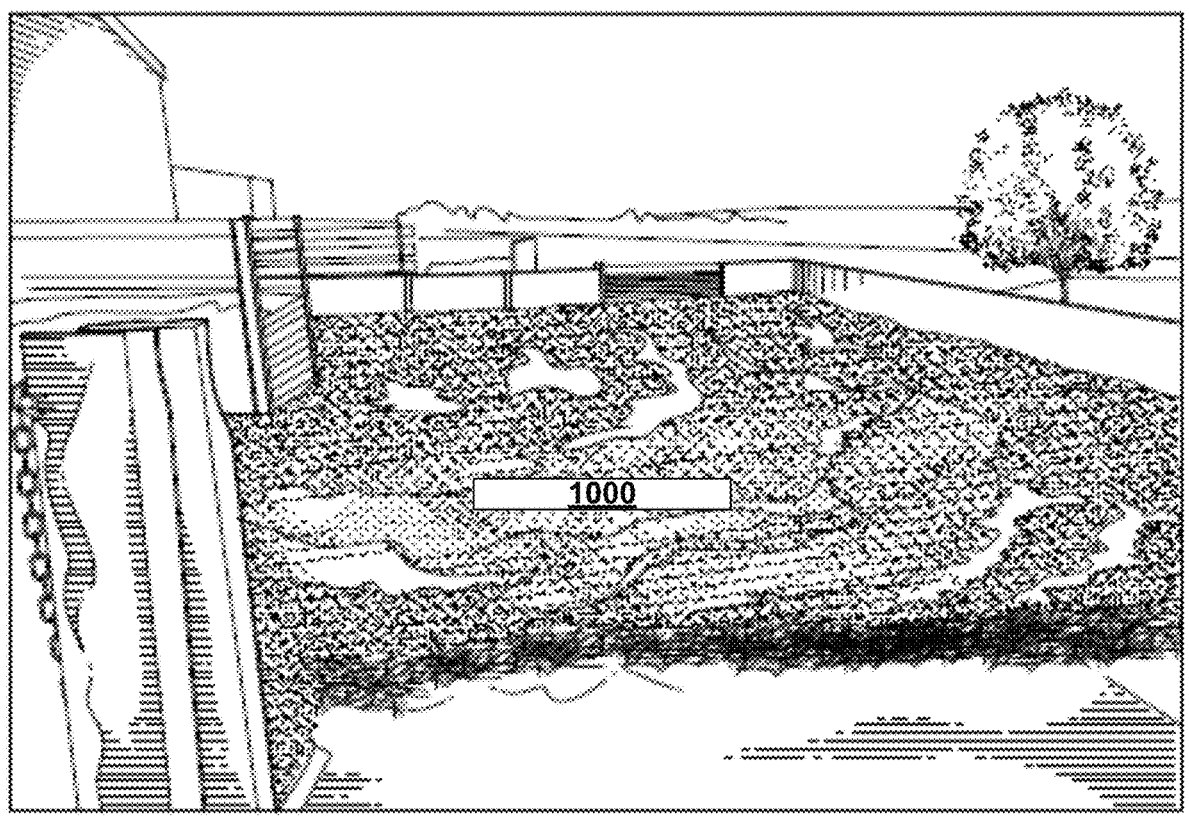
Figure 10B:
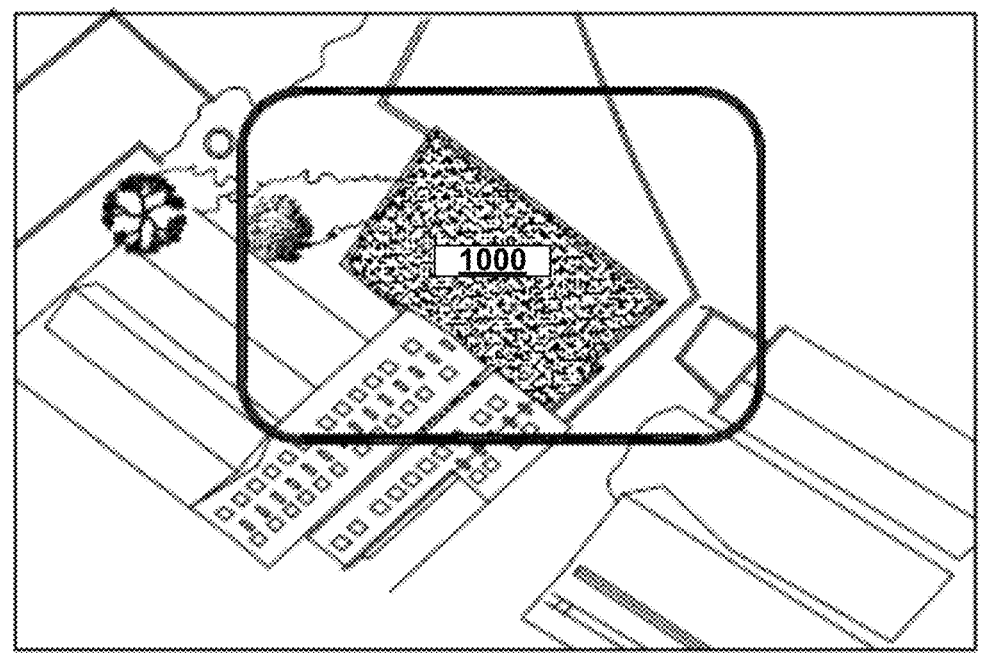

FIGS. 10A and 10B illustrate uncovered slurry lagoons.

Figure 11:
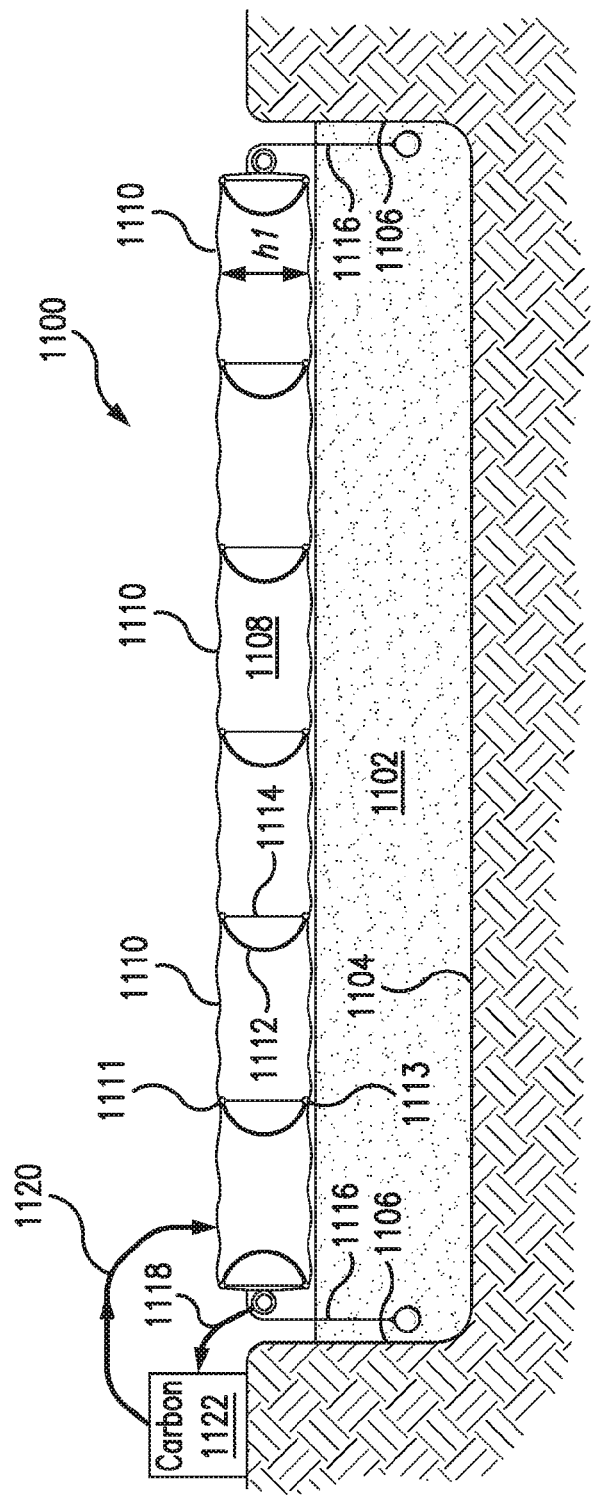

FIG. 11 illustrates a covered slurry lagoon system according to an embodiment.

Figure 12:
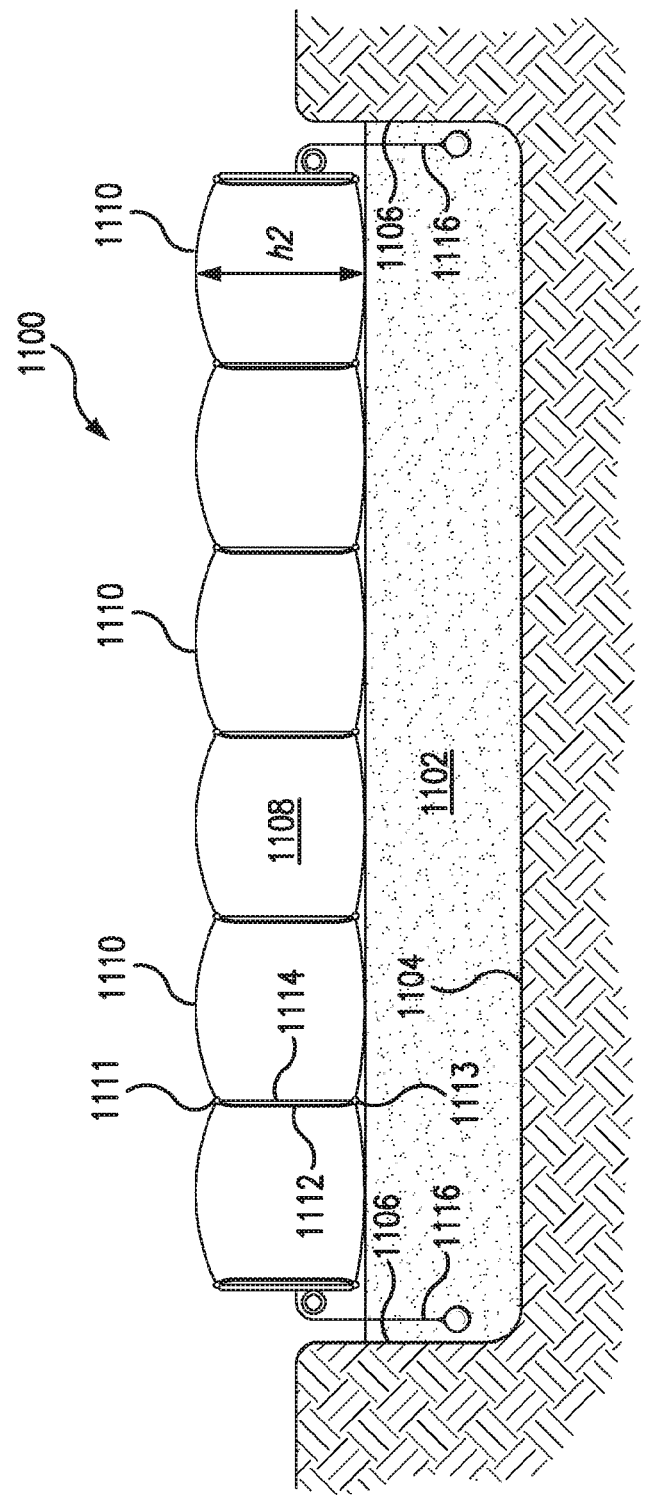

FIG. 12 illustrates a covered slurry lagoon system according to an embodiment.

Figure 13:
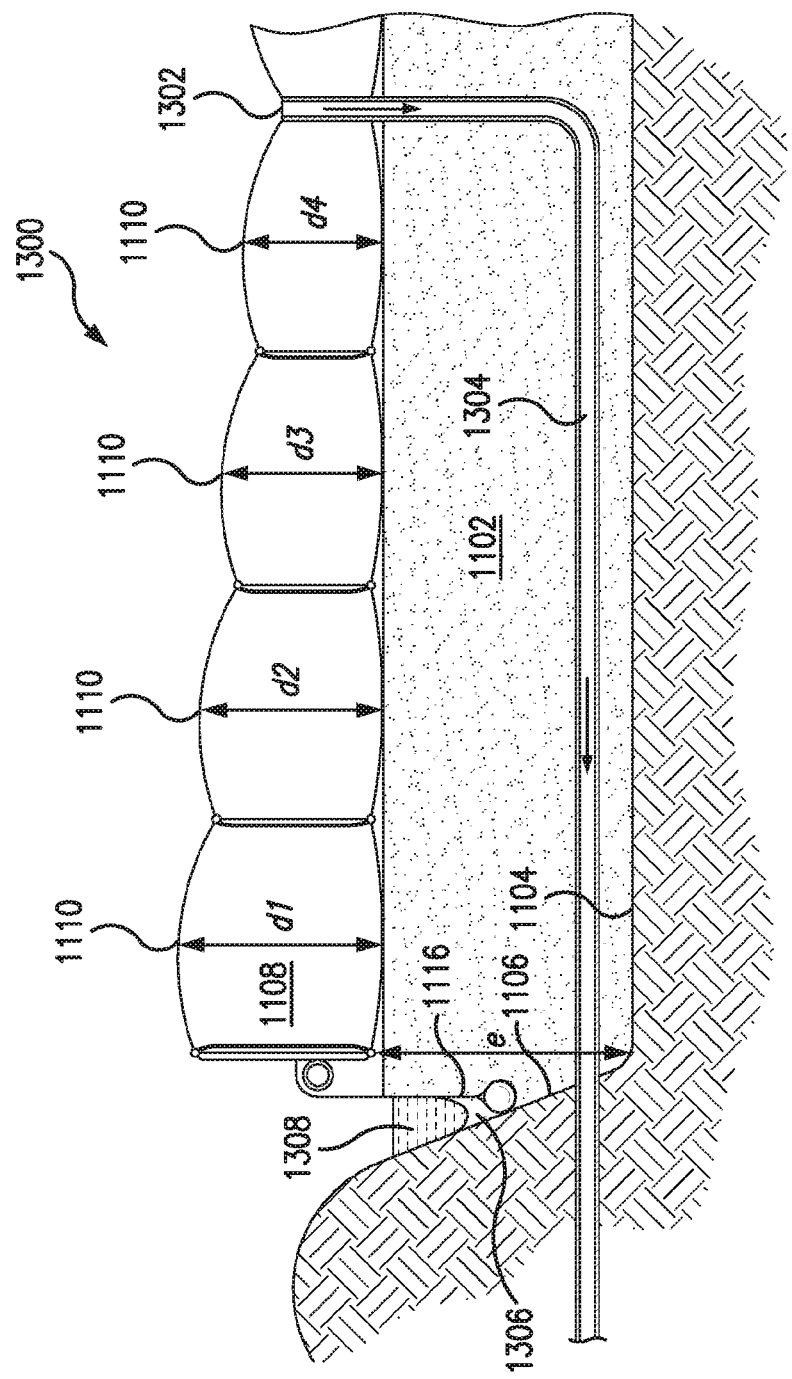

FIG. 13 illustrates a covered slurry lagoon system according to an embodiment.

Figure 14:
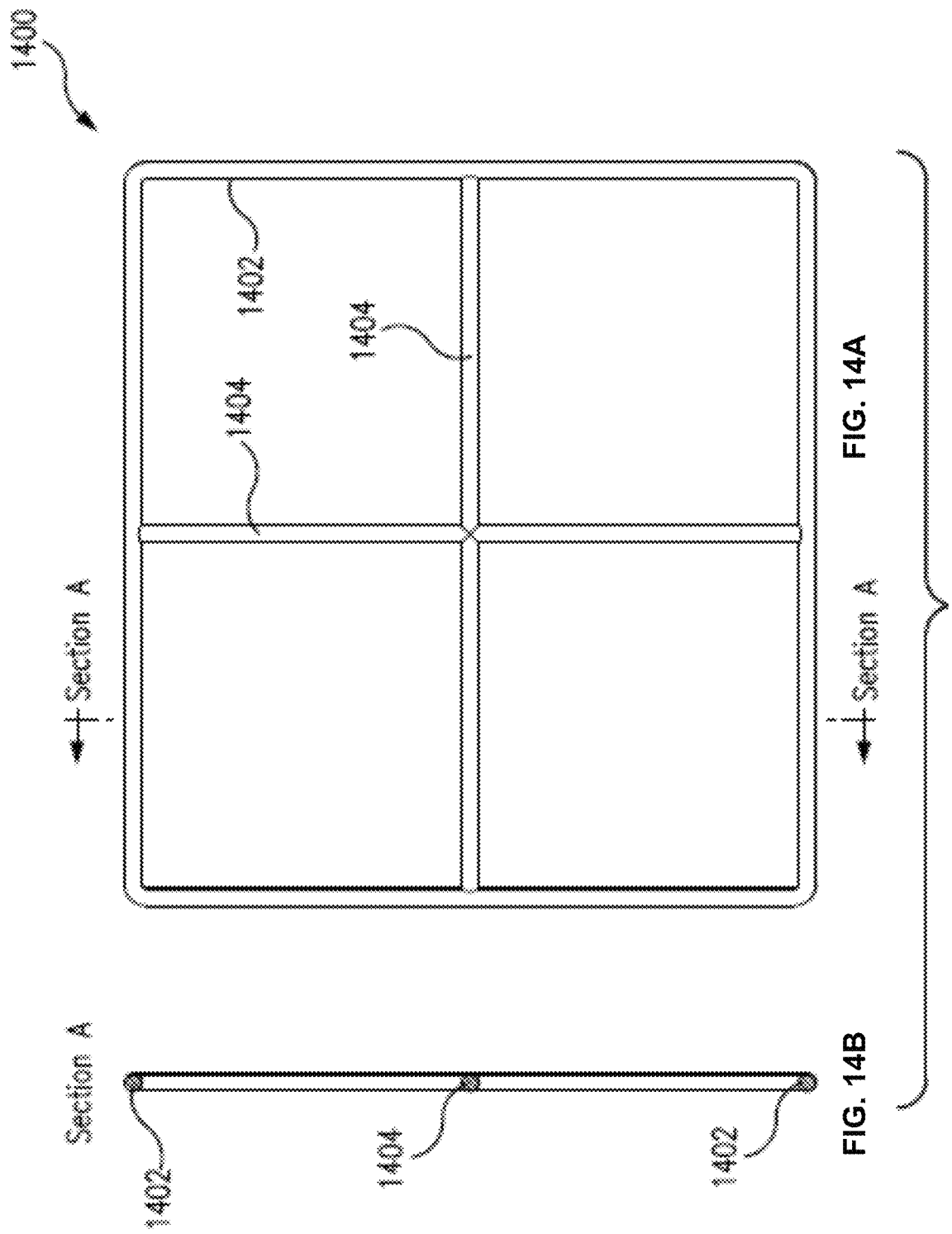

FIGS. 14A and 14B illustrate a rigid body according to an embodiment.

Figure 15:
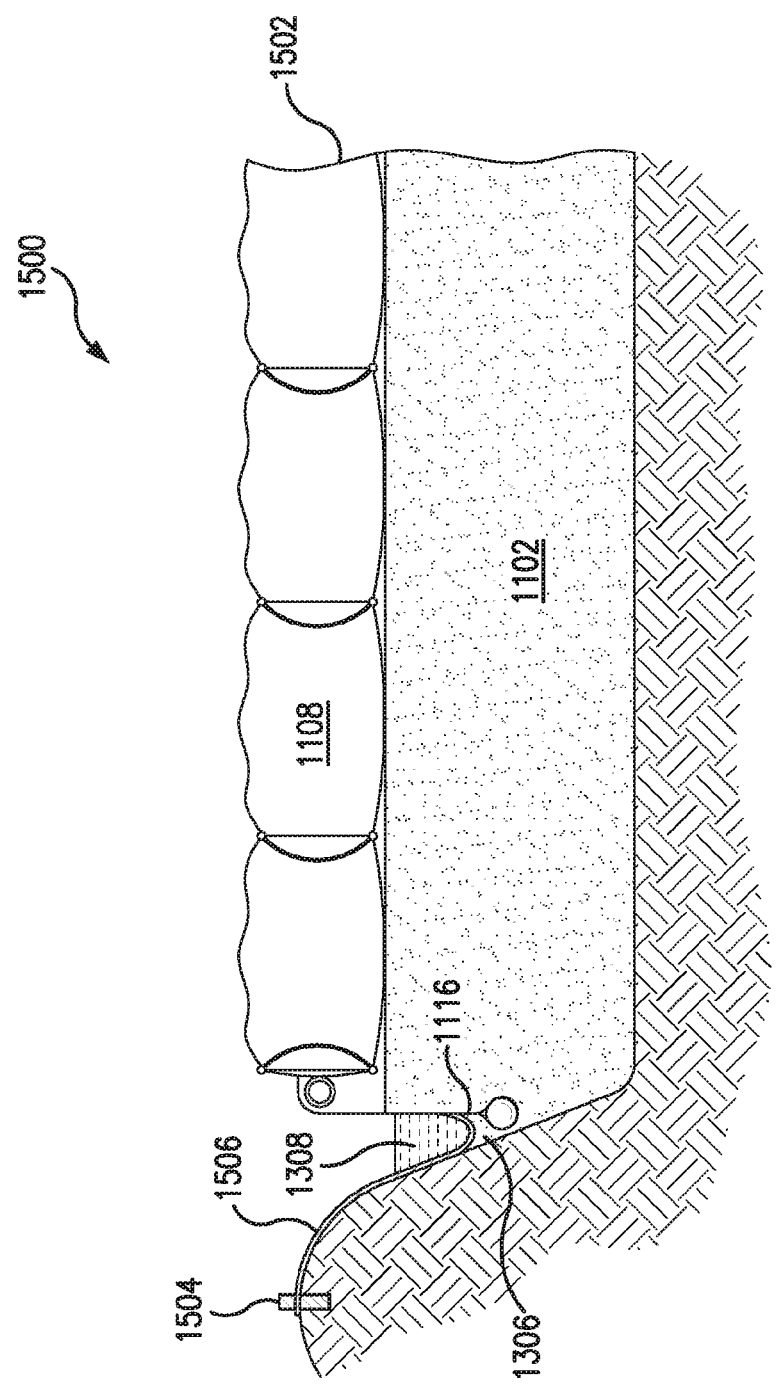

FIG. 15 illustrates a covered slurry lagoon system according to an embodiment.

Figure 16:
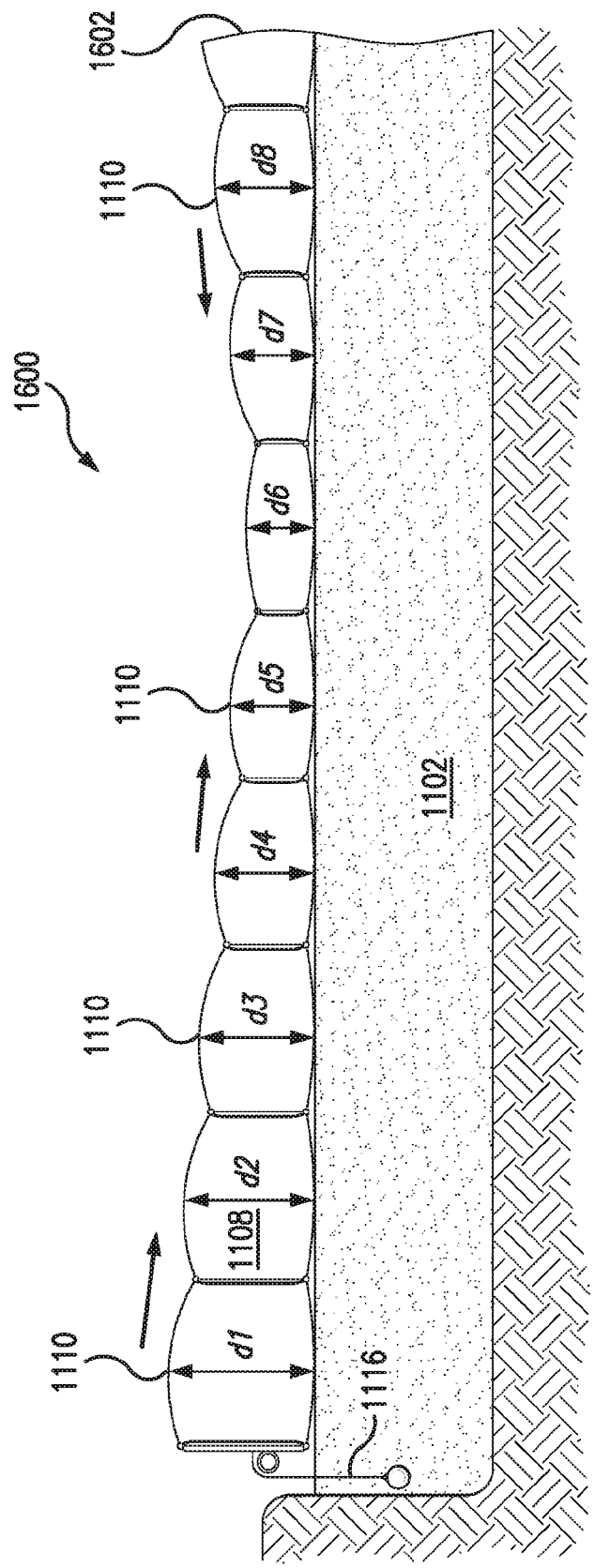

FIG. 16 illustrates a covered slurry lagoon system according to an embodiment.

Figure 17:
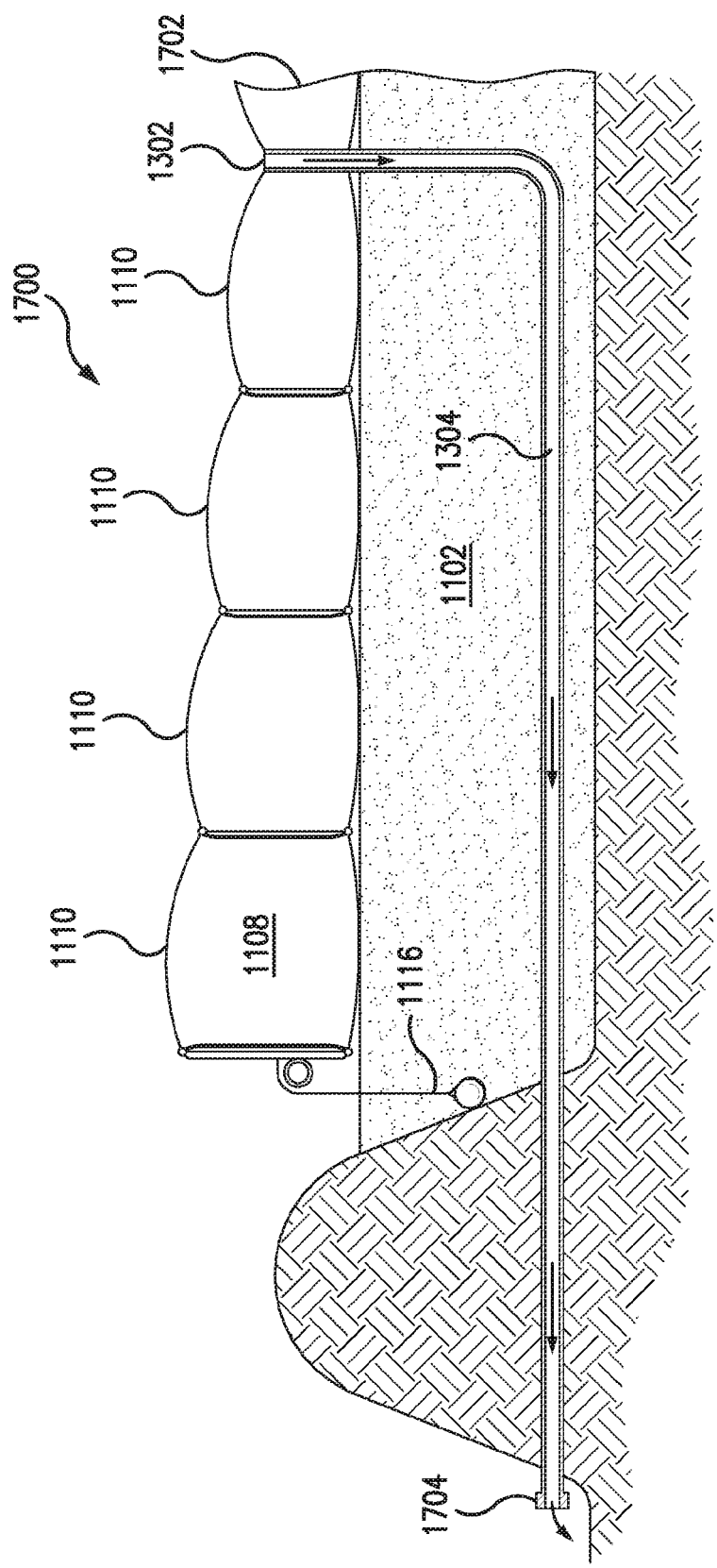

FIG. 17 illustrates a covered slurry lagoon system according to an embodiment.

Figure 18:
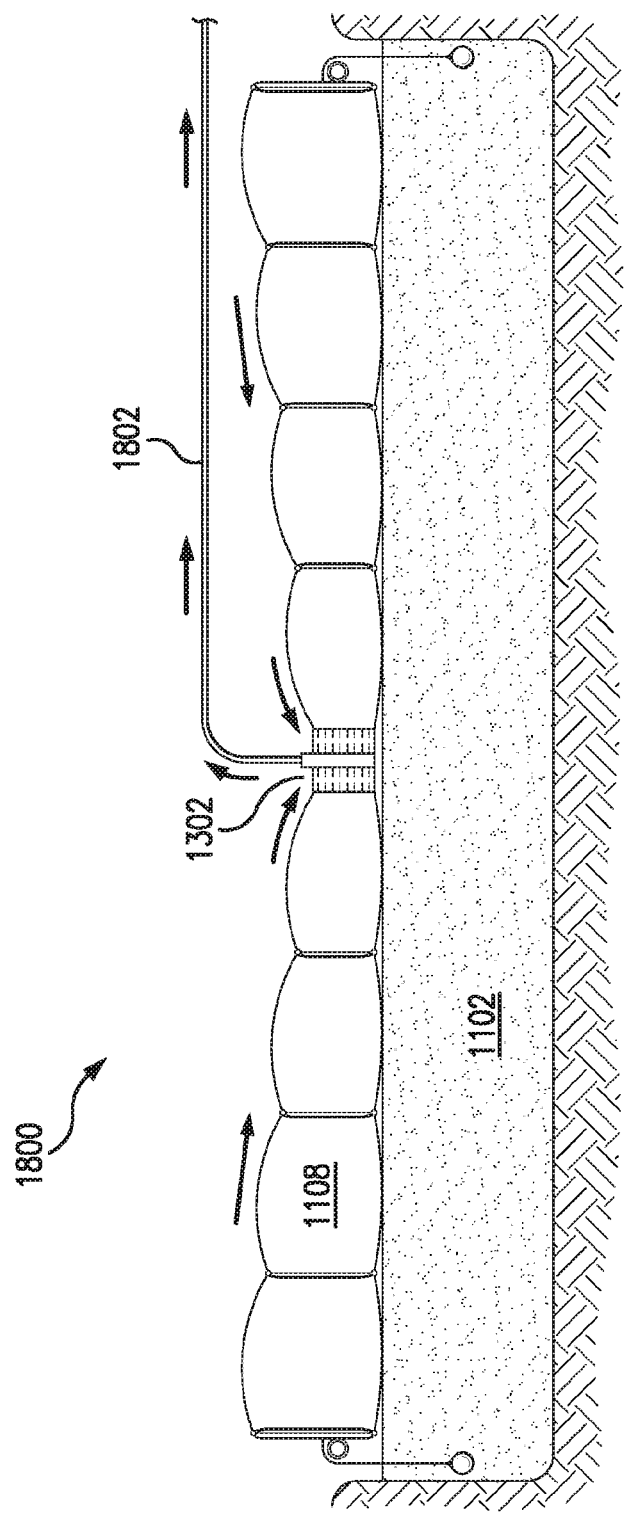

FIG. 18 illustrates a covered slurry lagoon system according to an embodiment.

Figure 19:
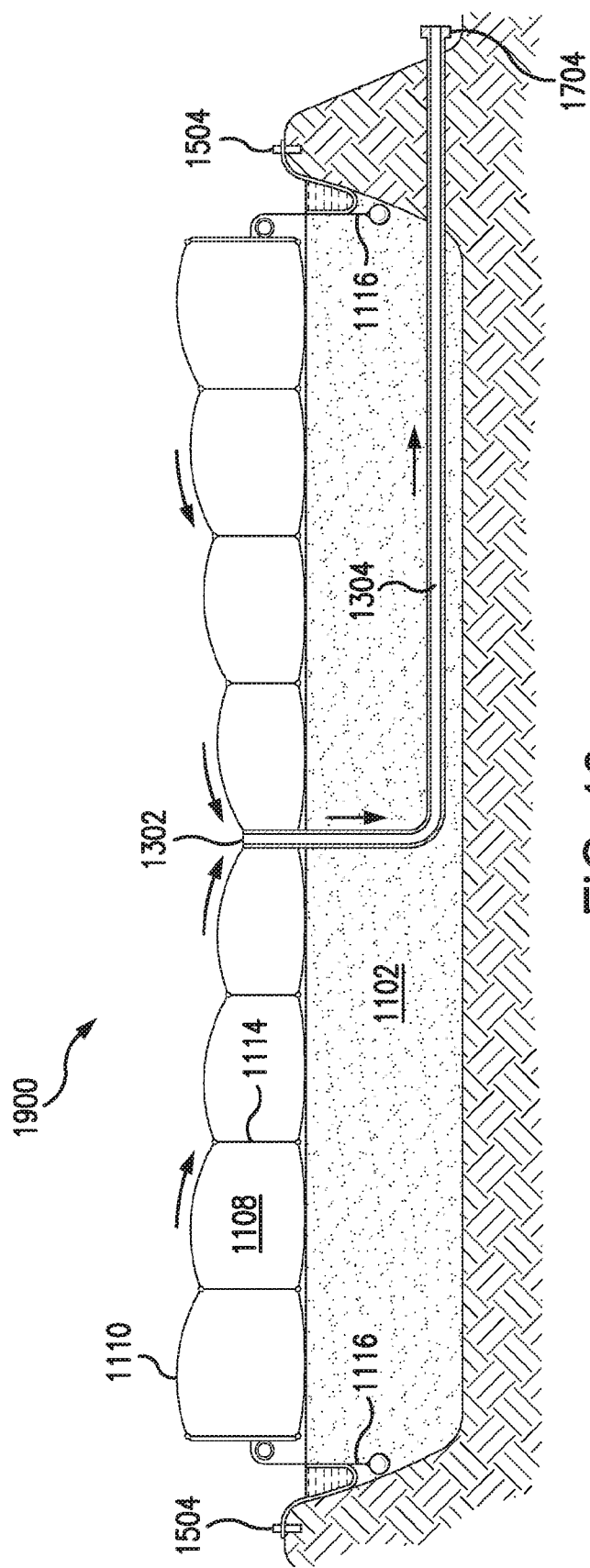

FIG. 19 illustrates a covered slurry lagoon system according to an embodiment.

Figure 20A:
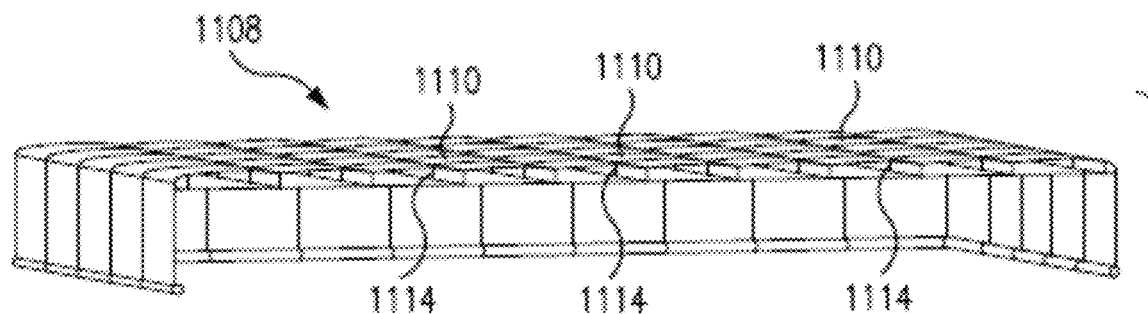
Figure 20B:
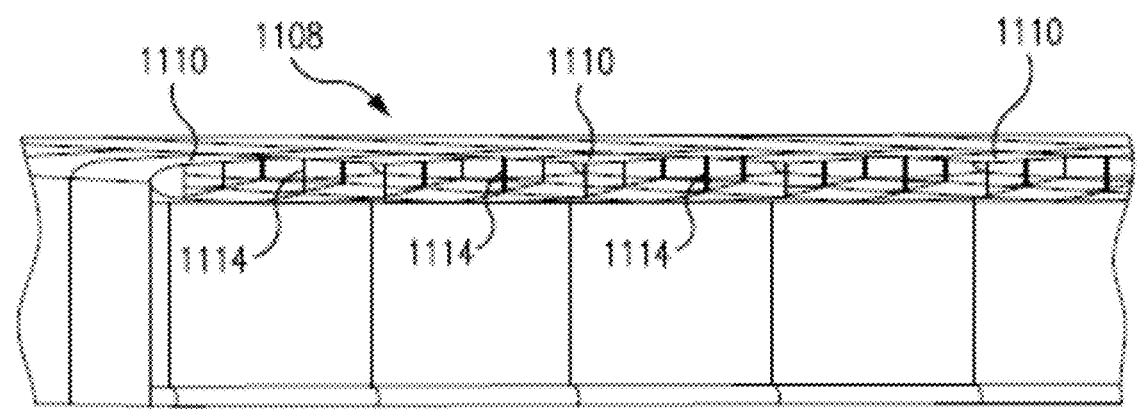

FIGS. 20A and 20B illustrate a cover according to an embodiment.

Figure 21A:
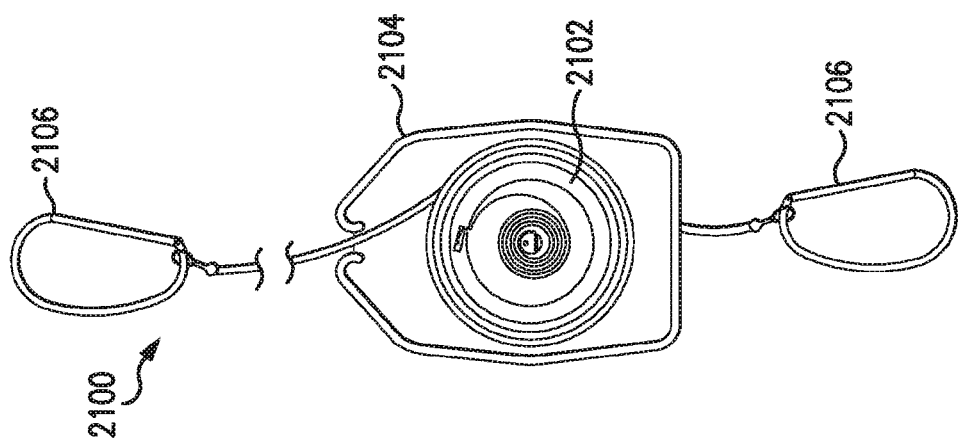
Figure 21B:
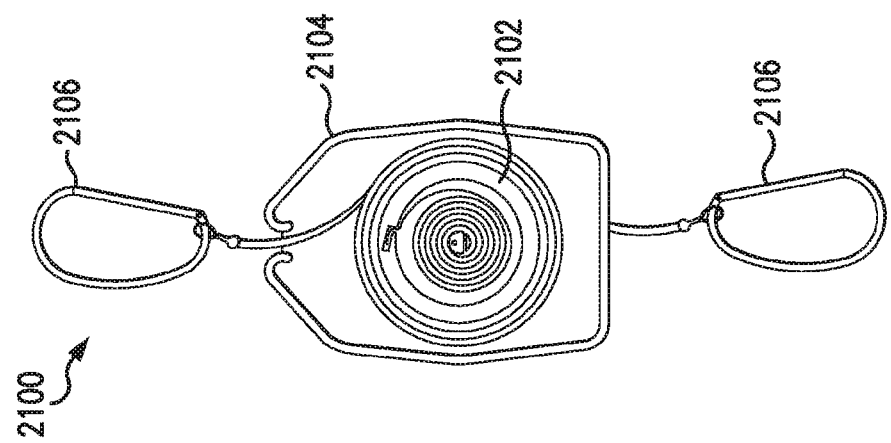

FIGS. 21A and 21B illustrate a clock spring with a rotary pulley system according to an embodiment.

DETAILED DESCRIPTION

While aspects of the subject matter of the present disclosure may be embodied in a variety of forms, the following description and accompanying drawings are merely intended to disclose some of these forms as specific examples of the subject matter. Accordingly, the subject matter of this disclosure is not intended to be limited to the forms or embodiments so described and illustrated.

Unless defined otherwise, all terms of art, notations and other technical terms or terminology used herein have the same meaning as is commonly understood by persons of ordinary skill in the art to which this disclosure belongs. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

Unless otherwise indicated or the context suggests otherwise, as used herein, "a" or "an" means "at least one" or "one or more."

This description may use relative spatial and/or orientation terms in describing the position and/or orientation of a component, apparatus, location, feature, or a portion thereof. Unless specifically stated, or otherwise dictated by the context of the description, such terms, including, without limitation, top, bottom, above, below, under, on top of, upper, lower, left of, right of, in front of, behind, next to, adjacent, between, horizontal, vertical, diagonal, longitudinal, transverse, radial, axial, etc., are used for convenience in referring to such component, apparatus, location, feature, or a portion thereof in the drawings and are not intended to be limiting.

Furthermore, unless otherwise stated, any specific dimensions mentioned in this description are merely representative of an exemplary implementation of a device embodying aspects of the disclosure and are not intended to be limiting.

As used herein, the term "adjacent" refers to being near or adjoining. Adjacent objects can be spaced apart from one another or can be in actual or direct contact with one another. In some instances, adjacent objects can be coupled to one another or can be formed integrally with one another.

As used herein, the terms "substantially" and "substantial" refer to a considerable degree or extent. When used in conjunction with, for example, an event, circumstance, characteristic, or property, the terms can refer to instances in which the event, circumstance, characteristic, or property occurs precisely as well as instances in which the event, circumstance, characteristic, or property occurs to a close approximation, such as accounting for typical tolerance levels or variability of the embodiments described herein.

Anaerobic Digestion

According to embodiments, many types of materials may be digested, including the anaerobic digestion of biomass. To achieve the most beneficial impact with respect to climate change, using anaerobic digestion to limit or eradicate "fugitive" emissions of methane (such as those that are currently created by the poor management of animal manures such as cow and pig slurry in open lagoons) may be most effective. Specifically, the use of open-slurry lagoons in the agriculture sector can result in very high levels of fugitive methane emissions. By sealing the slurry lagoon to prevent aerobic digestion, the methane can be contained. This practice can be advantageous for the purposes of limiting or eradicating "fugitive" emissions of methane, and in embodiments disclosed herein can also provide for considerable operational benefits. Such benefits may include reduced nitrogen loss where nitrogen is contained in the digestate (i.e., the material remaining after the anaerobic digestion of the biomass), which can in turn reduce the need for fertilizer when the digestate is spread back onto the land. Another benefit may include reduced handling and management of slurry. This is because rain water is prevented from entering the covered lagoon, meaning that the digestate is more concentrated and there is less to spread. Another benefit may be reduced risk of overspill because rain water is prevented from entering the covered lagoon, and in turn minimizes the possibility of leakage of raw slurry into waterways. Another benefit could include reduced greenhouse gases. Where biomass (such as waste or spoiled animal feed) is managed by composting aerobically and in an uncontrolled manner, the energy held in it is lost as heat during this process, and may result in large quantities of methane and nitrous oxides, both powerful greenhouse gases. Such greenhouse gases are reduced, however, with the use of a sealed slurry lagoon, such as provided by embodiments disclosed herein. Another benefit may be reduced energy demands. This is because anaerobically generated methane may be used as fuel for a generator, for instance to generate electricity and heat that can be used on the farm, thereby offsetting its electricity and energy usage. Where the installation cost of a covered slurry lagoon is kept low, for instance, the above benefits can provide a reasonable return on investment for small-to mid-sized farms as compared to an open slurry lagoon.

Excess methane derived from one or more embodiments can be used to generate power that is then injected into the electricity grid, or alternatively processed and upgraded for injection into the mains gas grid.

An abundant source of biomass is grass cuttings, such as on managed land including gardens, sports fields, roadside verges, and golf courses. Currently, either the grass cuttings are left where they fall or are collected and composted. Either way, this is carried out aerobically, thereby losing the methane generation potential as wasted heat. In addition, much of the northern hemisphere is covered in vast areas of unmanaged or under-utilized grassland that could be used to generate biomethane. As is the case with small, remote farms, however, it is difficult to realize the true value of methane producible through this process, due to, for instance, the remote location of manage or unmanaged grasslands, or the lack of electricity or gas-grid infrastructure. The financial and environmental value of this abundant form of renewable and zero carbon energy cannot be economically realized, leaving it effectively land-locked. Embodiments can address one or more of these issues.

Referring now to FIG. 1A, an anaerobic digestion system 100 is illustrated according to some embodiments. The system 100 may use, for instance, a biomass storage container 101. This could be, for example, a covered-lagoon arrangement having a lagoon with biomass storage 102 in the container. A gas cover 104 is also used, which may be a membrane. The lagoon may be built into the ground 112a, with an original ground level 112b. Although illustrated with an in-ground lagoon, other containers may be used to store biomass for digestion, including above-ground lagoons or other containment structures. The digestion of biomass within the container generates gas, which is trapped by cover 104. Additionally, and according to some embodiments, a slurry membrane (or separation liner) 106 may be used to separate the slurry region from the gas region and cover 104, thereby forming a buffer 116 between the cover 104 and biomass storage 102. In some embodiments, both the gas cover 104 and slurry separation liner 106 are non-permeable to the slurry and generated gas. In this respect, the gas buffer region 116 may be utilized by other system elements, such as energy storage and recovery system 126. In some embodiments, the slurry separation liner, or one or more additional membranes 138, may be semi-permeable for the selective passage of one or more materials (e.g., for selective passage of methane or $CO_2$). Region 116 may be above, below, or on both sides of the membrane 138 in embodiments, for instance, depending on the permeability of the membrane 138. Membrane(s) 138 may be optional in embodiments. In certain aspects, the container 101 (e.g., the lagoon) may further comprise a liner 114, which separates the biomass from the ground in which the lagoon is installed. According to some embodiments, one or more weights 108, 110 may be used on the surface of one or more membranes (e.g., cover 104 or separation liner 106). Such weights not only hold the membranes in place, thereby reducing fatigue and unwanted movement, but also can be configured to perform one or more additional functions, such as thermal management or level sensing. According to embodiments, thermal insulation may be used. For example, the cover 104 may provide thermal insulation.

In certain aspects, the digester is a biogas storage container with a semi-permeable membrane separating the biogas storage region into a first space and a second space, such that the first space is configured to be methane enriched and the second space is configured to be $CO_2$ enriched. The first and second space may be, for instance, on either side of membrane 138 in some embodiments. In some embodiments, the semi-permeable membrane comprises a stretched polytetrafluoroethylene-based material or silicone. In some embodiments, the cover positioned over the container is transparent, and is configured to provide passive solar heating (e.g., to the slurry). The cover can be made of numerous materials. In an example, the material is strong, chemically inert and immune to damage from ultraviolet light, such as Ethylene Tera Fluoro Ethylene (ETFE), though other materials may be suitable. While illustrated with a single semi-permeable membrane 138, multiple membranes may be used (e.g., 2, 3, 4, 5, etc.) in some embodiments, thereby creating more than two gas spaces. For example, there may be an additional membrane, and the first and second membranes would then separate the container into three spaces—a first space, second space, and third space that would contain more pure methane than the first space. One or more of the spaces formed by membranes (e.g., membrane 138) in the digestion system 100 can serve as a receiving or extracting spaces, for instance, when used as a buffer for an energy recovery and storage system. In some embodiments, it is the uppermost space (or whichever space comprises the cleanest biogas). In some embodiments, a gas processing (e.g., cleaning) system may draw from one or more of the spaces.

In certain aspects, the digestion system 100 may also include an input for receiving biomass (such as slurry) into the biomass storage container. Additionally, anaerobic digestion system 100 may include output valves coupled respectively to the second space and first space. That is, the biogas located within the biogas storage regions (e.g., in buffer 116) of digestion system 100 may be removed by pipes or hoses connecting to one or more of output valves. Such pipes and hoses may connect to one or more other systems described herein, including for gas processing, energy storage, and energy recovery. In embodiments, the second space and the remainder of the biomass storage container may be coextensive. That is, in some embodiments, there may be no physical separation between the biomass storage and the various gas regions.

Figure 2A:
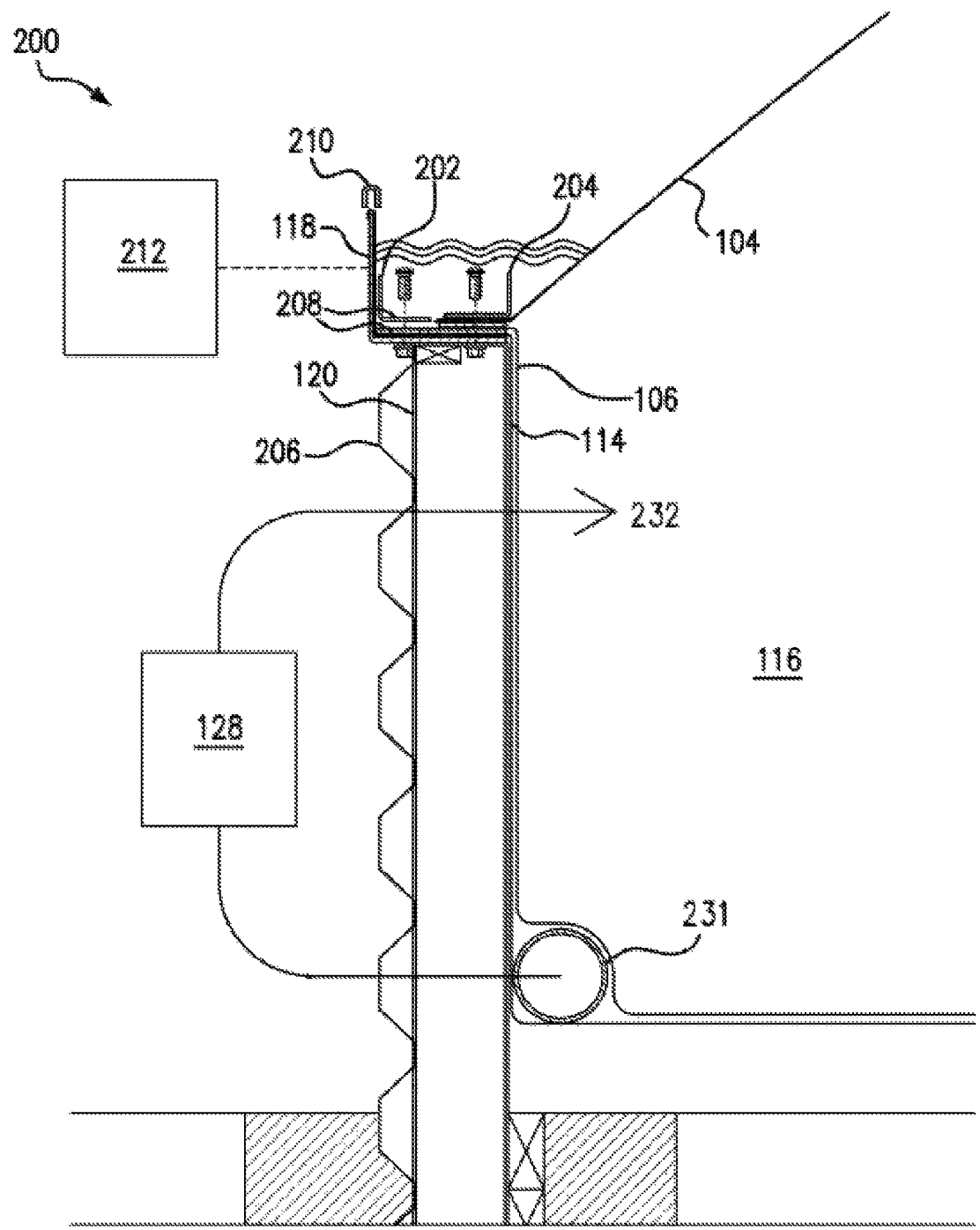
FIG. 2A illustrates aspects of an anaerobic digestion system according to some embodiments.

According to some embodiments, one or more of the gas cover 104, separation liner 106, any membranes 138, and lagoon liner 114 are held in place by a bracket element 118. Bracket 118 may be mounted, for instance, to an installation post 120 in ground 112b. The bracket 118 may be a portion of a beam. In certain aspects, the bracket 118 shown in FIGS. 1 and 2 is a cross-section of a beam. Use of a bracket 118 or beam (e.g., similar to a steel Z purlin used in construction) can be used to form a water collection region 122, in which water (e.g., rain or snow) from the cover 104 is collected. According to embodiments, the bracket 118 (e.g., beam portion) has at least one 90 degree angle, or approximately 90 degree angle surface, such that it provides a mounting surface for one or more L-shaped claims. The bracket 118 (e.g., beam portion) may be L-shaped. In certain aspects, an angled beam may form a gutter that tracks the outer ring of the lagoon. That is, it may be a gutter ring beam. The collected water can then be re-used by one or more systems, as described in connection with FIG. 2A. Moreover, by preventing the water from reaching the biomass storage, the necessary size of the lagoon can be minimized by eliminating dilution of the slurry (e.g., of storage 102). This can also help prevent unwanted spillage of slurry from excess rain. The collection of water in region 122 can have the additional benefit of covering one or more gas seals, such as the seals where cover 104, slurry membrane 106, and/or liner 114 are connected. When filled with water, the collection region 122 permits the monitoring and detection of leaks in the seals. For example, if gas were to escape the seals, it would form bubbles in the water collection region 122 that would be visibly or audibly detectable.

In certain aspects, the lagoon cover 104 eliminates the extra capacity needed to cope with and store rainfall on the lagoon. The rainfall on an open lagoon has the effect of diluting the contents—the extra volume has to be accommodated in a larger sized lagoon.

According to embodiments, the system 100 can include one or more additional subsystems. This could include, for instance, thermal management 124, energy storage and recovery 126, gas processing 128, and slurry mixing 130. Gas processing 128 may include, for instance, the extraction of gas from the biomass storage region 102 to the gas buffer 116 under cover 104. This is further illustrated, for instance, in FIGS. 2A and 2B, in which sour gas is extracted through a pipe (e.g., pipe 231) from the slurry storage region 102, processed, and moved to buffer 116 as refined biogas (e.g., 232). The pipe (or other extraction means) can be located between the lagoon liner 114 and slurry cover 106, for example. In some embodiments, the gas processing may further include cleaning or compression of the extracted gas. This could include, for instance, one or more of removal of hydrogen sulfide via filtering (e.g., hydrogen sulfide generated in small quantities as part of the anaerobic digestion process), cooling or heating of the gas, and extraction of $CO_2$ in either liquid or solid form. According to embodiments, thermal management 124, energy storage and recovery 126, and gas processing 128 may be part of the same unit or sub-system, or separately provided. With respect to thermal management 124, in some embodiments, water-filled weight tubes on a membrane (e.g., cover 104 or slurry liner 106) can be connected as a water circulation system and used to either direct solar heated water down into a slurry region (e.g., a slurry membrane pea gravel thermal store) to increase the temperature (and hence increase the speed) of the anaerobic digestion process, or, filled with heated water to prevent build-up of ice and snow in the pleats of a membrane (e.g., cover 104).

With respect to slurry mixing plant 130, embodiments may include an in/out pipe 132a; one or more mixing pipes 132b and 132c; and one or more angled mixing elements 134. According to embodiments, the mixing elements 134 are angled relative to the base of the lagoon, and can have an angle that matches the angle of the sides of the lagoon in the slurry region 102. In certain aspects, the mixing plant 130 may perform, or otherwise be part of, a thermal management system. In some embodiments, the mixing plant 130 contains one or more sensors for monitoring the temperature or pH of the slurry. For instance, the slurry may flow past one or more of such sensors, for instance, mounted within the plant 130 housing or the mixing pipes. Such information can be used for control of the overall system 100.

Referring now to FIG. 1B, an alternative illustration of an anaerobic digestion system 100 is provided according to some embodiments, which includes a resource-neutral bunded lagoon 166 that extends above and below an original ground level. For example, the lagoon is dug into the natural earth with the internal contents banked so that the sides are tapered. An advantage of this arrangement is that no earth has to be removed from the site. In this respect, the biomass container (e.g., container 101) may be formed partially or entirely by dirt, including natural earth. In certain aspects, the sloping slides can be thermally insulated to improve the performance of the slurry lagoon, and further, the lagoon itself may be lined with an impermeable membrane. Such thermal insulation may be provided by a cladding (e.g., on an installation post or lagoon sidewall), the lagoon liner, or both. In addition to potential thermal management, an additional layer (e.g., adjacent the lagoon liner) may further protect the lagoon liner from materials in the soil. In some embodiments, the slurry 162 within the pit is covered by a slurry separation liner 106, which keeps it separate from a gas region 116 on the top of the pit. In this example, a gas membrane or cover 104 and a slurry separation liner form a gas buffer 116. Additionally, the gas membrane and slurry separation liner may be provided with water or gravel filled tubes, which serve as weights (e.g., 108, 110). One or more gas and/or thermal processing elements are also shown on either side of the lagoon. In some embodiments, a plant room (e.g., plant 130) houses one or more systems for stirring the slurry in the lagoon below the separation liner, for instance, using an in/out pipe 132a and one or more stirring elements 134. In some embodiments, stirring elements 134 comprise a pressurized nozzle.

Referring now to FIG. 2A, aspects of a water and gas management subsystems 200 of an anaerobic digestion system, such as system 100, are shown according to some embodiments. For examples, certain water management aspects of the system 100 are illustrated, as well as one or more connections of elements and/or gas processing. As shown in FIG. 2A, water (e.g., rain water or snow) may collect in the water collection region (e.g., region 122 of FIG. 1A). In certain aspects, the water in collection region 122 covers one or more gas seals used to assemble the lagoon. This could include, for instance, the seals of the cover 104, slurry covering membrane 106, and lagoon liner 114. In some embodiments, all gas seals are covered by the collection region 122. In this respect, the water itself can be utilized as a monitoring device. For instance, if there are any leaks in the gas seal bubbles may be visible or audible. Bubbles may be detected, for example, using one or more microphones installed in the water collection region.

Figure 2B:
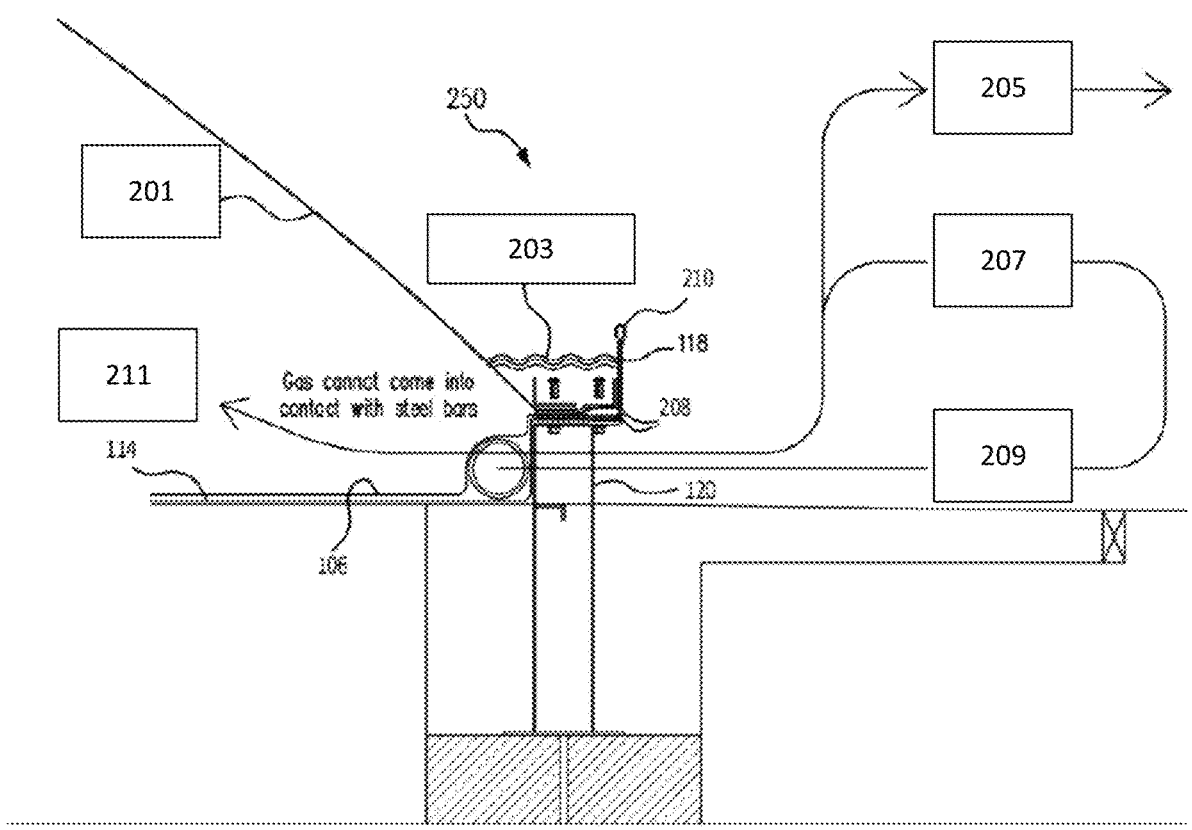
FIG. 2B illustrates aspects of an anaerobic digestion system according to some embodiments.

As shown in FIG. 2A, an installation post 120 is used in some embodiments. For instance, a post 120 can be sunk into the banked earth adjacent the lagoon to provide a support for the components above the lagoon, including one or more mounting surfaces. The post 120 may be formed, for example, of galvanized steel. In some embodiments, the post 120 may include a cladding layer 206, for instance, for thermal management. With respect to installation, a hole can be excavated for each support post 120. In this example, the hole is cleaned out, and the base is tamped down. Each hole then has a datum pin driven into the centre of the base of the pit to a set level. Concrete is poured and flattened "level" with the top of the pin, which forms a concrete pit base on which the posts stand while the ring beam is being erected and lined up to ensure alignment. When the ring beam is positioned correctly, a small amount of concrete is poured around the base of each post to fix it in position (e.g., as illustrated in FIG. 2B). When the concrete perimeter path is poured, the remainder of the post pit is filled and concrete then encases the post and ties in the bottom lip of the gutter ring beam.

As further shown in FIG. 2A, and according to some embodiments, the water management aspects of system 100 may also comprise a secondary water system 212. Water collected in collection region 122 may be diverted to the secondary system, which may could include a water storage tank, washing station, livestock watering system, irrigation system, or the like. Diverted water from the covered lagoon rain handling system should be clean, and thus, can be stored and used for myriad purposes such as parlor wash down, livestock drinking water, irrigation, etc. Water may be provided to the secondary system/storage 212 using one or more pipes, hoses, and a pump. Additionally, gravity may be utilized for moving the water from the lagoon area to the secondary system 212. According to some embodiments, the material used for the cover 104 is safe for use with potable water.

According to embodiments, a membrane clip strip 210 may be used to connect edge portions of liner 114 (or any other membrane) to an upper edge of the bracket 118. Additionally, an outer membrane clamp 202 and an inner membrane clamp 204 may be used to secure one or more of the gas cover 104, separation liner 106, and lagoon liner 104 to the installation post 120. The clamps may have, for instance, an "L" shape. In some embodiments, the shape of the clamps (alone or taken together) match the shape of a water collection region. In some embodiments, the seal can be improved with one or more gaskets 208 (e.g., PVC closed cell foam gaskets). The arrangement of water and gas management subsystems 200 of FIG. 2A can beneficially: (1) cover all gas seals with water; and (2) prevent the biogas from coming into contact with one or more vulnerable parts, such as steel components of the anaerobic digestion system 100. For instance, exposure to biogas may corrode steel components. According to embodiments, an installation post 120 may include one or more nuts (e.g., captive m 10 riv nuts) as mounting points for a gutter ring beam.

According to embodiments, sour gas can be extracted from pipe 231 (e.g., from a slurry region), processed by system 128, and returned to a gas storage region as refined gas 232.

Referring now to FIG. 2B, an alternative illustration 250 of aspects of an anaerobic digestion system 100 is provided according to some embodiments, including one more of connection of elements, water management, and gas processing. According to some embodiments, sealing of the top cover keeps all metal parts away from biogas. For instance, the sealing of the top cover inside a manufactured trench around the lagoon can keep corrosive gases from the slurry pit away from the metal parts, potentially extending the life of the lagoon and reducing necessary maintenance. Although sour gas is illustrated as extracted from a region below separation liner 106, in some embodiments, it may be extracted from other regions, such as a region below one or more membranes 138. The location of the extraction pipe (or other device, including one or more valves) may be arranged to accommodate extraction from any gas region. In some embodiments, gas may be extracted, filtered or otherwise cleaned, and returned to another gas region of the digester. In some embodiments, gas (e.g., refined gas) may be extracted and fed to a processing system for liquefaction, storage, etc. A gas membrane storage 201, rainwater management system 203 that covers all gas seals, a gas processing system 205, a gas filtration system 207, sour gas extraction 209, and refined biogass 211 are also illustrated in FIG. 2B.

Figure 3:
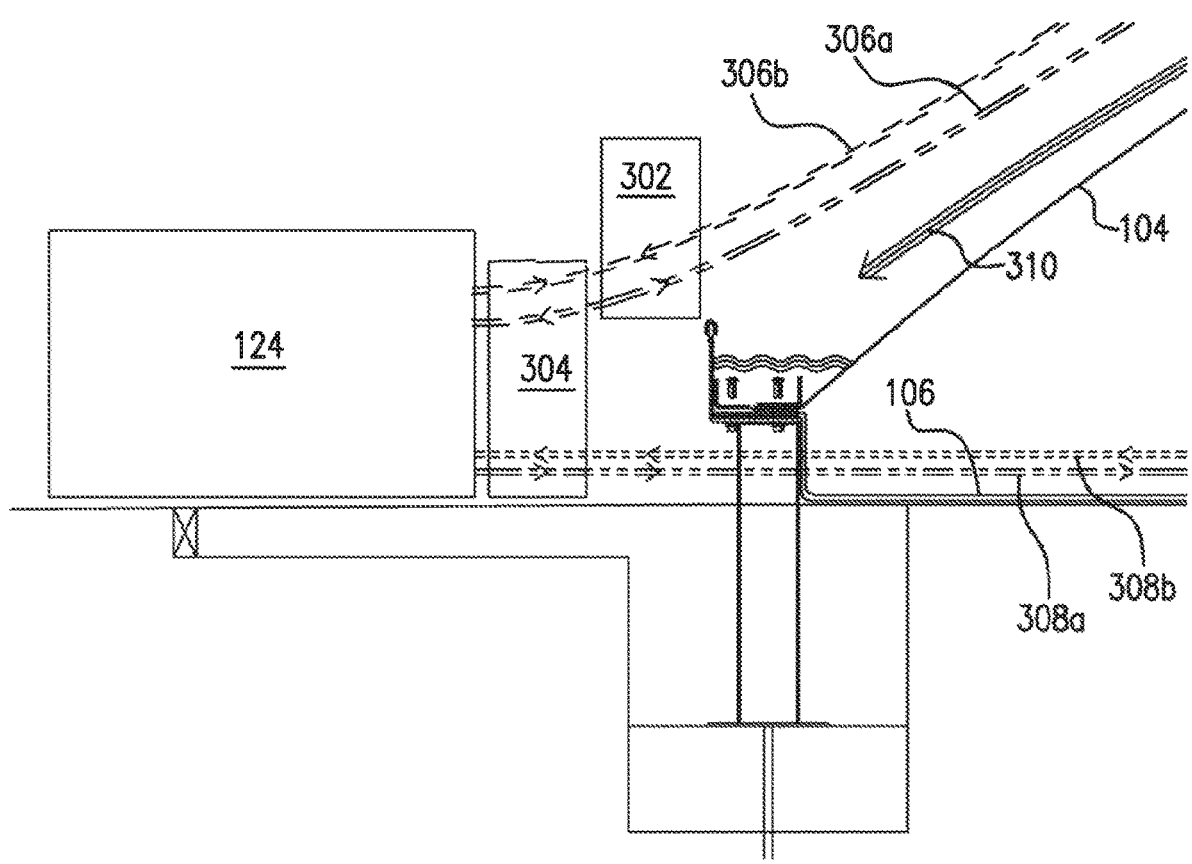
FIG. 3 illustrates a thermal management system according to some embodiments.

Referring now to FIG. 3, aspects of a thermal management system, such as system 124 of anaerobic digestion system 100, are illustrated according to some embodiments. In some embodiments, the system can be used to melt snow/ice off the surface of the lagoon cover by circulating heated water or water heat-exchanged with the lagoon. In some embodiments, for instance on a hot or sunny day, the water can be circulated over the cover and subsequently used to heat the lagoon, raising the biogas yield.

In embodiments, system 124 may function as a heating system (e.g., a closed loop heating system), in which solar-heated water from gas cover 104 (e.g., through weight tubes, such as weights 108) can be circulated to or through to slurry, such as slurry membrane 106 (e.g., through weight tubes, such as weights 110) to heat the biomass storage 102 of a lagoon. Similarly, hot water from a system process (e.g., anaerobic digestion in the lagoon) can be circulated to/or through the gas cover (e.g., through weight tubes) to prevent build-up of snow or ice, which can damage the system 100. In this respect, system 124 may include one or more ice/snow defrosting circuits 302, and a slurry heating circuit 304. These circuits may be internal or external to a housing of system 124, for instance integrated into one or more tubes/piping or not, and may be co-located or separately located from each other. According to embodiments, one or more of the circuits comprises a loop of tubing together with a pump and a heating element. The heating element may be fed, for instance, from either waste electricity or waste heat from another process, either directly or indirectly via a heat exchanger. In this example, hot water may be circulated (e.g., using a pump) to or from the cover 104 via tube or pipe/tube 306a, while tube or pipe 306b is used for cold water. Similarly, hot water may be circulated to or from the slurry membrane 106 via tube or pipe 308a, while tube or pipe 308b is used for cold water. While illustrated with different pipes/tubes, a single pipe/tube may be used in some embodiments. Additionally, where different pipes/tubes are used, such piping may be dedicated based on direction as opposed to temperature. For both 306 and 308, the water may be moved through a weighted tube as described elsewhere in this disclosure. That is, a weighted tube may be used for multiple purposes, including stabilizing a cover (e.g., 104 or 106) while also moving water for thermal management of the system 100. In some embodiments, rainwater management 310 can be used to move water from cover 104. This could be, for instance, flowed through a weight, the collection or runoff, or utilize a pump. In some embodiments, excess rainwater is pumped off from a top of gas cover 104 to collection region 122, or vice-versa.

Figure 4A:
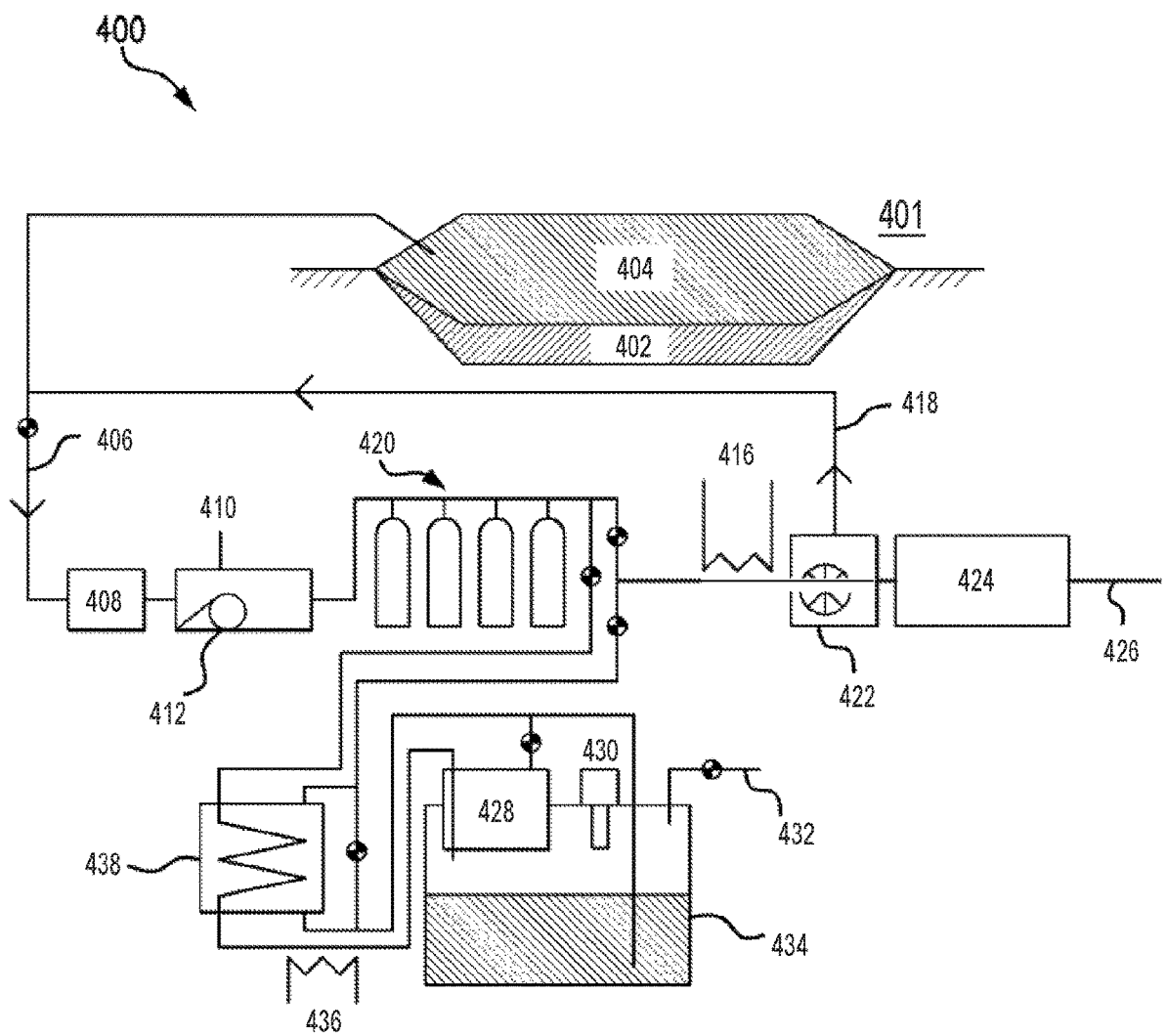
FIG. 4A illustrates an energy storage and recovery system according to some embodiments.
Figure 4B:
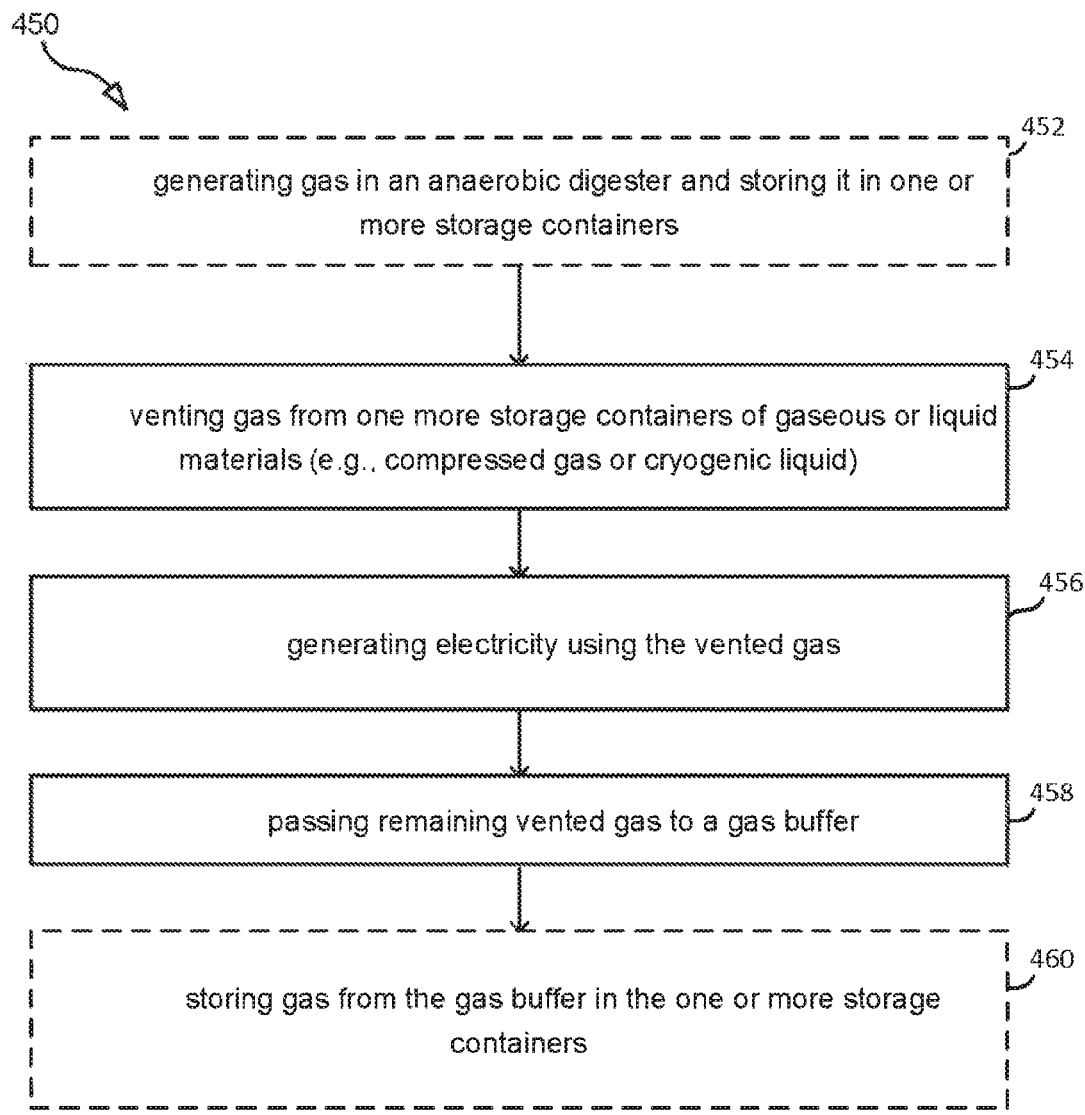
FIG. 4B is a flow chart of a method for energy recovery according to some embodiments.

Referring now to FIGS. 4A and 4B, aspects of a gas buffer storage and/or energy recovery system are illustrated according to some embodiments. Such storage and energy recovery may be combined with one or more embodiments described herein, including anaerobic digestion system 100. As an example, an energy storage and recovery system 400 can be used to process and store biogas from system 100, use the stored biogas to generate electricity, and then pass the used biogas back to the system 100. The process may be repeated, for instance, based on the availability of energy from other sources, such as photovoltaics and wind energy devices. This may be a cost-effective alternative to using batteries, which can be expensive relative to other components. In some instances, disclosed systems may eliminate the need for using batteries for substantial energy storage. However, the energy storage and recovery systems disclosed herein may be used in conjunction with one or more batteries. While described in connection with an anaerobic digester, according to embodiments, system 400 and related methods may be implemented using a buffer that is not part of digestion system 100.

As shown in FIG. 4A, a gas buffer storage element 404 can be used as part of an energy storage and recovery system 400. According to embodiments, such a gas buffer may be part of anaerobic digestion system 100. For example, it may be part of a digester 401 with biomass storage 402 (e.g., a covered lagoon with slurry). In a mixed electricity generating system having one or more of photovoltaics and wind energy, an energy store can be an important buffer to the system when energy from such sources is not available. An alternative or an adjunct to such a mixed system is storing materials (e.g., methane), either as a cryogenic liquid or gas pressurized in gas bottles, according to some embodiments. As an example, the methane 406 in a buffer store (e.g., methane that would have otherwise been fugitive methane but has been captured) can be compressed into high pressure bottles when there is a plentiful supply of electricity. As another example, the methane can be liquefied when there is a plentiful supply of electricity, and similarly stored. That is, the plentiful supply of electricity may be used to power a storage system (e.g., power one or more compressors or other liquefaction stages) to store gas in high pressure bottles or cryogenically store a liquid. An example of a suitable material is methane; however, other materials such as hydrogen or $CO_2$ may be used. When the supply of electricity is low or the demand for energy is high, the stored material (e.g., gaseous or liquid methane) can be released through a gas-powered generator 422, such as a turbine, to generate electricity (either directly or indirectly by using an additional stage to create electricity from the gas-powered generator). After processing to generate electricity, the exhaust gas 418 can be released back into the buffer store (e.g., buffer 116 of system 100), where it is ready for re-cycling or further processing. A benefit of this approach is that it is a cost-effective means of storing energy and harvesting electrical energy when it is plentiful. As part of the biogas refining process, the compressor and bottle store may be already available, and thus, the only additional component needed is the turbine or other gas-driven generator.

According to embodiments, system 400 may include a covered slurry lagoon digester 401 comprising a slurry stored in biomass storage 402 and a gas buffer storage element 404, for example, as described with respect to FIGS. 1A and 1B and system 100. The gas buffer region in this example may be a separate gas bag or storage unit according to some embodiments. The gas may be passed to bottle storage 420 (e.g., compressed gas or cryogenic liquid storage). Prior to storage, the gas may be processed. This could include, for instance, passing the gas through a dryer 408 and/or compressor 412 (e.g., running on AC power 410). Other processing may be used, such as filtering, cooling, etc. As needed, for example on-demand, energy may be recovered from the stored gas/liquid by passing it to a recovery stage. According to embodiments, the recovery stage comprises a gas pressure driven electrical generator. In some embodiments, the gas is heated 416 (e.g., by an electric heating element) prior to the electrical generation. The heating may be used, for instance, to increase its volume of the gas, thereby increasing the power from the turbine. The generated electricity may be conditioned 424 and output as AC electricity 426 (e.g., to mains electric). The gas used by the generator may be passed as exhaust 418 back to a storage element. This could include a buffer storage, or back to the bottles of the bottle store. In some cases, the buffer storage may be part of the anaerobic digester, such as system 100. This could include, for example, the region 116 or a separate gas bag dedicate to use for energy recovery.

System 400 may further include one or more elements for cleaning or liquefaction of gas (e.g., methane) for cryogenic storage. This may include, for instance, the use of a cold store 438 or other cooler 436. A liquefier element 428 can convert gas from the gas buffer or bottle storage to liquid form (e.g., convert methane gas to liquid methane) using one or more cooling/refrigeration components, such as a Joule Thompson unit, other cryocoolers (e.g., a Sterling cooler), a sacrificial liquid (e.g., liquid nitrogen), or Brayton cycle device. Additionally, one or more cooling stages may be cascaded. An additional cooling element (e.g., a Sterling cooler 430) can be used to reduce the overall temperature of a liquid storage vessel 434. In the example of FIG. 4A, the flow of liquid and/or gas may be controlled by one or more valves. A Dewar pressure raising element 432 may be used such that liquid methane can be driven out of the Dewar for use or storage. The liquefaction elements can be used to process gas from the buffer store, the exhaust of the generator, and/or a bottle store to generate liquids, such as liquid methane. Such liquids may similarly be passed back to a bottle store (e.g., 420). According to embodiments, the storage, cleaning, and/or liquefaction stage may be a storage, liquefaction, and/or cleaning stage as described with respect to FIGS. 9, 9A, 9B, and/or 9C.

According to embodiments, system 400 may further include one or more processing and control components, such as apparatus 500. Such processing and control components can be used to monitor the availability of energy from other sources (e.g., photovoltaic or wind), receive communications for on-demand processing, open or close one or more connected valves (e.g., to vent gas from storage) of the system 400, monitor storage levels, and activate elements (e.g., a generator or compressor). In embodiments, one or more steps of process 450 may be responsive to or otherwise based on such monitoring and/or communications. For example, the system may be configured to store energy (e.g., in bottle storage) when energy is available from other sources, and generate energy (e.g., with a generator) when energy from other sources is not available. Such actions may be taken by activating one or more components of system 400, for instance, in response to an indication by apparatus 500.

Referring now to FIG. 4B, a process 450 for gas storage and energy recovery is provided according to some embodiments. The process may be performed, for instance, by system 100 and/or 400.

In some embodiments, the process may optionally begin with step 452, in which gas is generated in an anaerobic digester (e.g., system 100) and then stored in one or more storage containers. Such storage containers may include, for instance, high pressure gas storage and/or cryogenic liquid storage. The storage step may include cleaning, compression, and/or liquefaction of biogas. While anaerobic digestion is used as an example, the energy recovery process 450 may be used with stored gaseous or liquid materials derived from other sources. That is, system 400 and process 450 are not limited to biogas in all embodiments. According to embodiments, one or more aspects of step 452 may be based on and/or responsive to the availability or price of energy from other sources (e.g., photovoltaic, wind, mains electric).

Step 454 comprises venting gas from one more storage containers of gaseous or liquid materials (e.g., compressed gas or cryogenic liquid such as methane). In some embodiments, the gas is biogas.

Step 456 comprises generating electricity using the vented gas. This may include, for instance, passing the vented gas through a turbine. According to embodiments, one or more of the venting (454) and generating (456) can be based on the availability of energy from another source, such as a battery, photovoltaic, and/or wind-driven device. In certain aspects, gas venting can be used to generate electricity when other sources are unavailable or inefficient. Conversely, gas may be stored (e.g., step 452 or 460) when power from such other sources is readily available. In this respect, power generation, storage, and recovery may be optimized as needed.

Step 458 comprises passing the remaining vented gas to a gas buffer. This may include, for instance, passing the gas back to a buffer storage associated with an anaerobic digestion system 100, or otherwise coupled to storage (e.g., bottle storage as shown in FIG. 4A). For example, the gas may be stored between the gas cover/membrane 104 and the slurry cover membrane 106. An additional membrane or storage area may also be used, which can be kept deflated until needed to store the used exhaust gas of process 400.

In step 460, which may be optional in some embodiments, gas from the gas buffer is stored in the one or more storage containers. According to embodiments, the process 450 may be repeated as needed. That is, gas may be compressed and stored, used to generate electricity, then re-compressed and re-stored as needed.

According to embodiments, a system or method for taking a cryogenic liquid and converting it to a gas at, or around, room temperature allows energy recovery on three levels. Firstly, the expansion of the gas (from the conversion of the liquid to the gaseous phase) is fed through a pneumatic generator for the generation of power. Secondly waste heat can be used to augment that process and increase the volumetric expansion ratio. Thirdly the methane gas can be used in an internal combustion (IC) engine to create additional power. In some embodiments, the third aspect can be omitted, and the gas returned to storage where it can either stay until required and used in an IC engine or used for other purposes. According to embodiments, this may be accomplished with the system 400, which can include an IC engine.

Figure 5A:
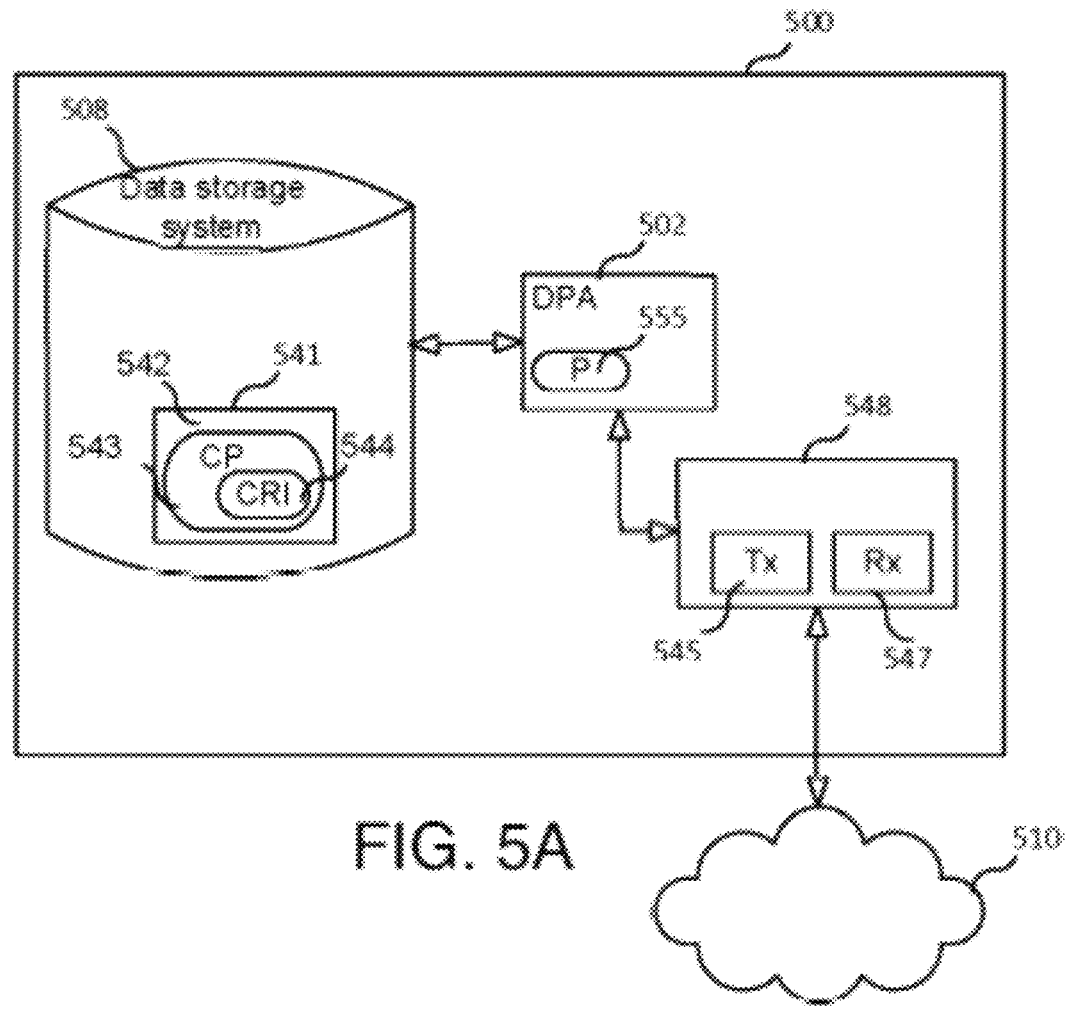
FIG. 5A illustrates a block diagram of an apparatus according to some embodiments.
Figure 5B:
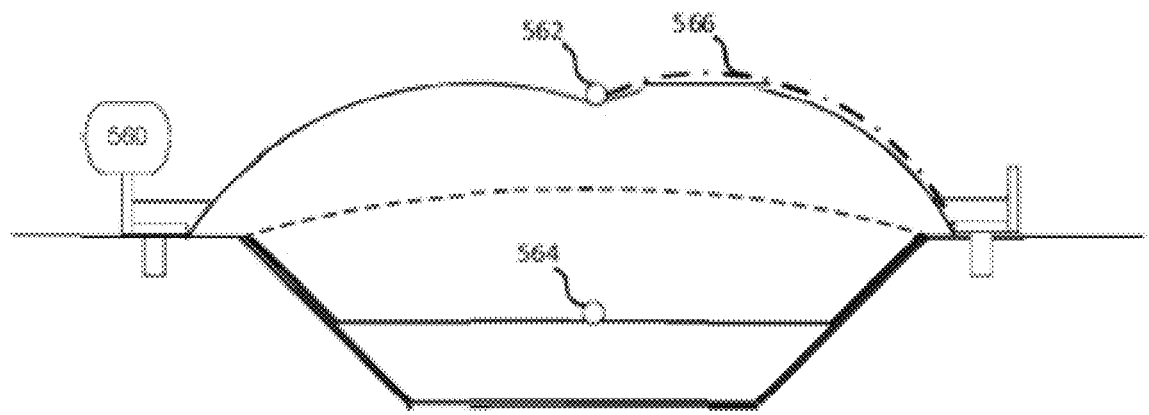
FIG. 5B illustrates aspects of an anaerobic digestion system according to some embodiments.

Referring now to FIGS. 5A and 5B, one or more gas level monitoring systems are illustrated according to some embodiments. In certain aspects, the condition of a lagoon or anaerobic digestion system, such as system 100, can be remotely monitored. Remote monitoring and sensing of the fill state of the lagoon (e.g., in terms of the amount of slurry and/or the amount of biogas) may be used as part of automatic control of an anaerobic digestion process. Examples of monitoring may include the use of, for instance, one or more of the following.

A water head—an end (e.g., the bottom) of one or more water filled weight tubes on a gas cover (e.g., cover 104 or slurry membrane 106) can be fitted with pressure sensors to measure the water head pressure. As the gas store fills, the center of the gas membrane is lifted and the water head increases. Similarly, as a slurry level decreases, the slurry membrane drops and the water head decreases. The system can be calibrated to calculate the amount of gas building up in the store or slurry available or digestion, e.g., using apparatus 500 of FIG. 5A.

Line of sight device(s)—a camera can be mounted and calibrated to monitor the top level of the gas or slurry membrane. Such monitoring can use multiple cameras at different levels and locations. Again, the results may be processed by apparatus 500, for instance, using computer vision techniques of filtering by colour hue and/or shape detection to map image pixel key-points to geometric feature points. In certain aspects, prominent shapes of conspicuous colour can be adhered to the cover or coloured objects placed behind to enable key-points of height and angle to be determined due to their presence, invisibility, or perspective in the images captured. That is, a cover or other membrane may comprise a prominent geometric shape or pattern or shapes, including at least one shape of a different color than the cover or membrane.

A sensor array—a festoon string array of sensors (e.g., gyroscopic accelerometers or angular sensors) can be used on the surface of a membrane (e.g., gas cover 104 or slurry membrane 106). Such an array may run, for instance, from a gutter (e.g., water confinement region) to the center of a gas membrane. A cross section of the inflation profile may be determined from modelling the cover shape by interpolating the inflation angle between known points where angular measurements exist. As the membrane moves (e.g., rises or falls), the string or sensors will similarly move. The movement can be calibrated such that it is associated with a particular level, and processed by apparatus 500.

FIG. 5A illustrates a block diagram of an apparatus 500 (such as associated with an anaerobic digester system 100 or related logistics coordination, such as an coordination center) according to some embodiments. As shown in FIG. 5A, the apparatus may comprise: processing circuitry (PC) 502, which may include one or more processors (P) 555 (e.g., a general purpose microprocessor and/or one or more other processors, such as an application specific integrated circuit (ASIC), field-programmable gate arrays (FPGAs), and the like); a network interface 548 comprising a transmitter (Tx) 545 and a receiver (Rx) 547 for enabling the apparatus to transmit data to and receive data from other nodes connected to a network 510 (e.g., an Internet Protocol (IP) network) to which network interface 548 is connected; and a local storage unit (a.k.a., "data storage system") 508, which may include one or more non-volatile storage devices and/or one or more volatile storage devices. In embodiments where PC 502 includes a programmable processor, a computer program product (CPP) 541 may be provided. CPP 541 includes a computer readable medium (CRM) 542 storing a computer program (CP) 543 comprising computer readable instructions (CRI) 544. CRM 542 may be a non-transitory computer readable medium, such as, magnetic media (e.g., a hard disk), optical media, memory devices (e.g., random access memory, flash memory), and the like. In some embodiments, the CRI 544 of computer program 543 is configured such that when executed by PC 502, the CRI causes the apparatus to perform steps described herein (e.g., steps described herein with reference to the flow charts). In other embodiments, the apparatus may be configured to perform steps described herein without the need for code. That is, for example, PC 502 may consist merely of one or more ASICs. Hence, the features of the embodiments described herein may be implemented in hardware and/or software. While discussed in connection with level sensing, apparatus 500 may be used in connection with other embodiments disclosed herein, including for management of an energy storage and recovery, control of a thermal process, remote operation of one or more components of the system 100, or for networked communication of system status.

Referring now to FIG. 5B, an anaerobic digestion system with one or more monitoring devices is provided according to some embodiments (e.g., level or pressure sensing). In this example, the monitoring devices comprise one or more line of sight cameras 560, a string of sensors 566, and one or more pressure sensor weights 562, 564. The pressure sensors may be mounted, for instance, as part of a weighted tube used for a gas membrane (e.g., a gas cover or slurry cover as described with respect to system 100).

Figure 6A:
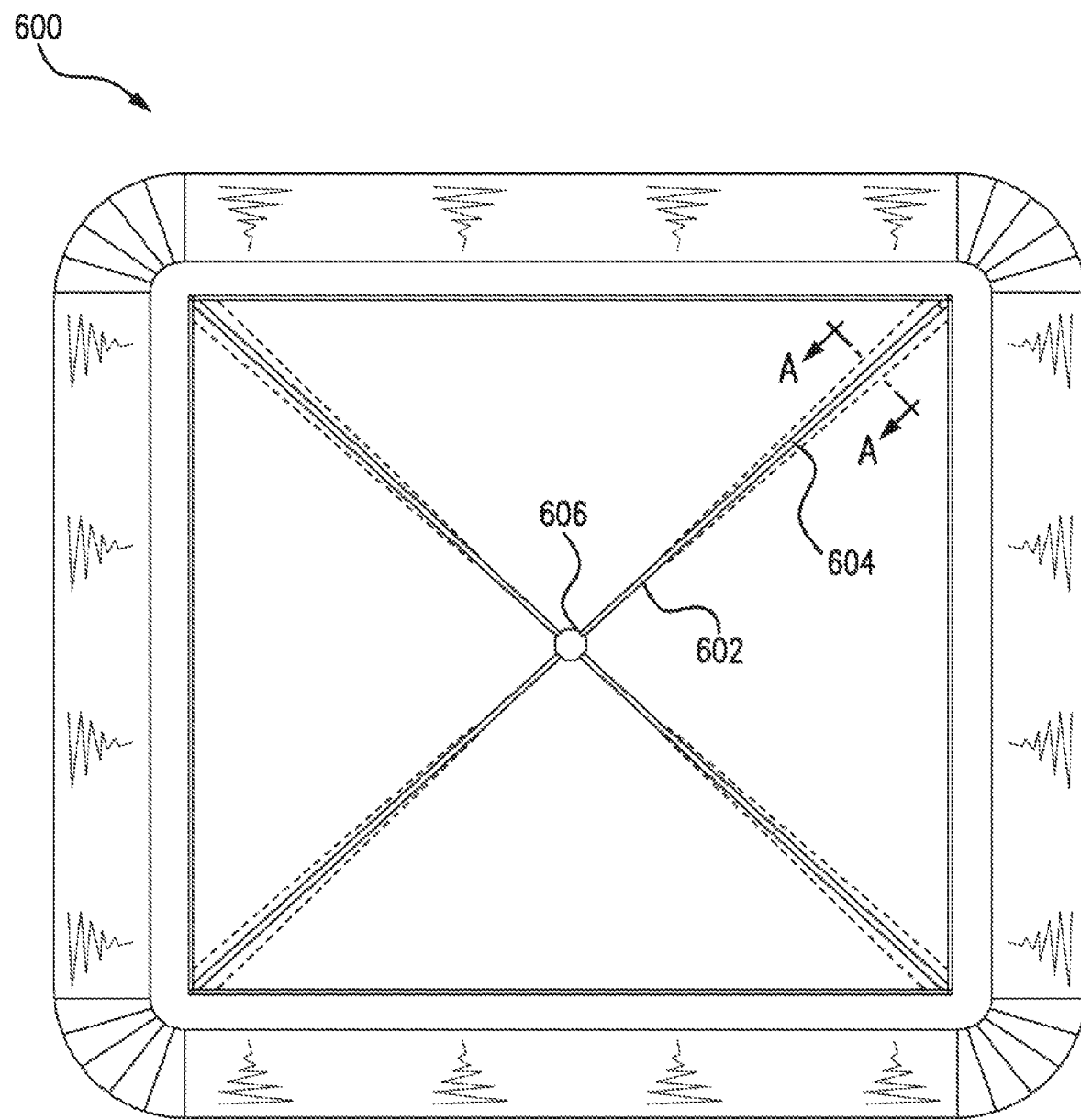
FIGS. 6A and 6B illustrate a cover for an anaerobic digester according to some embodiments.
Figure 6B:
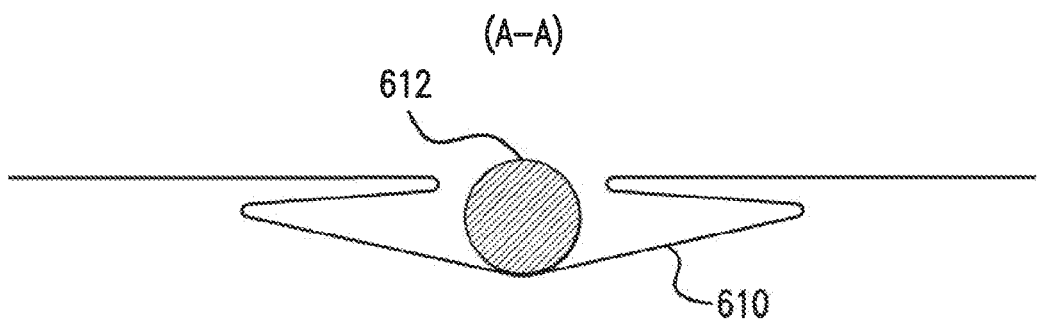

Referring now to FIGS. 6A and 6B, a pleated cover 600 designed for a covered lagoon, such as may be used in system 100, is illustrated according to some embodiments. In this example, a gas membrane is shown in plan view. In some embodiments, the pleated corner design of a gas membrane (or slurry membrane) can allow the cover to be made entirely in the workshop with no need for any field seams. In certain aspects, water-filled weight tubes (or other elongated weighted elements) can create tension on the membrane to prevent flapping of the cover in the wind. This can prevent damage, and also reduce fatigue failure of the cover.

Figure 7:
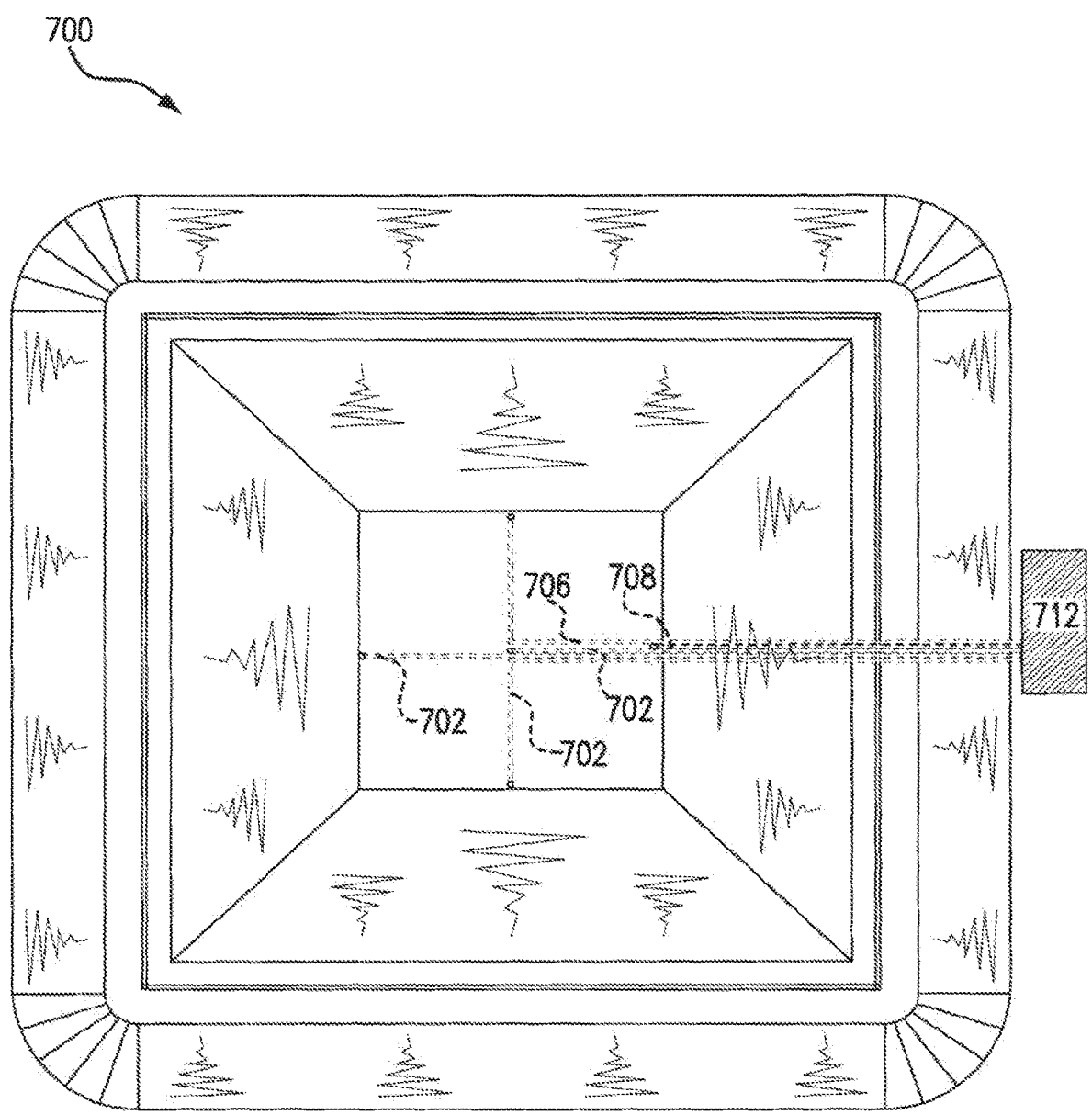
FIG. 7 illustrates a lagoon with one or more elements for mixing and/or heating of slurry.

Referring now to FIG. 6A, a cover 600 for a lagoon cover is illustrated according to some embodiments. This could be used, or instance, in system 100. In this example, one or more weights 602 and 606 may be used. According to embodiments, weight 602 is a weighted tube/pipe. For instance, it could be filled (or fillable) with water or another material, such as gravel. Weight 606 could be, for instance, a center weight bag. In certain aspects, the weights 602 may create one or more pleated corners 604. FIG. 6B shows a cross-section of a pleated corner along line A-A. In this example, a tube 612 is shown (e.g., a water filled weight tube) where a pair of folds 610 are formed (e.g., gas membrane folded pleats). According to embodiments, the folded pleats run at an angle of 45 degrees from the corners of the ring beam. As an example, on a square lagoon, they could meet (or nearly meet) when folded. In this embodiment, the center weight bag could also have a square shape, with sides aligned to the lagoon's sides. As another example, for a rectangular lagoon, the center weight would be longer in one dimension by the difference between the width and length of the ring beam forming the sides of the lagoon, where the long side of the weight bag would be aligned with the long side of the lagoon. Similarly, the central weight 606 could be a weight tube. According to embodiments, a gas membrane of an anaerobic digestion system (e.g., cover 104 or slurry membrane 106 of system 100) can be made from a polymer material, such as fabric-reinforced polymer sheeting, including a fabric covered by a polymer material. Examples include the XR® membrane materials provided by Seaman Corporation, which is classified as an Ethylene Interpolymer Alloy (EIA), or the POLYPLAN biogas membranes provided by Sattler Pro-Tex GMBH. In some embodiments, the cover is transparent and is configured to provide solar heating for the anaerobic digester Referring now to FIG. 7, lagoon design 700 (e.g., a lagoon excavation plan) is provided according to some embodiments. In this example, a plant 712 comprises a pipe to I/O and pipes 702, 706, and 708, which are connected to mixing elements. According to embodiments, the design 700 may be used in system 100. For instance, the mixing elements may correspond to element 134 shown in FIG. 1A, and the pipes 702, 706, and 708 may correspond to elements 132*a-c*.

Figure 8:
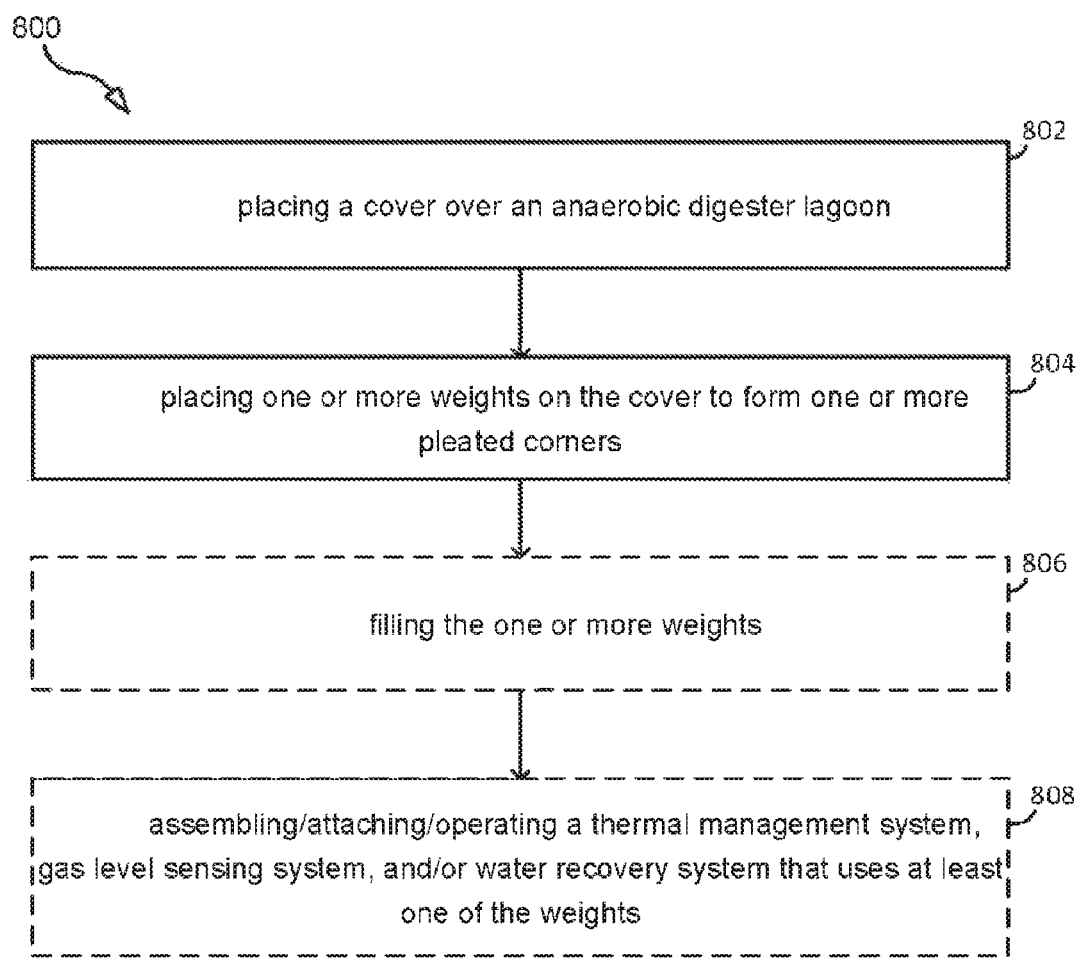
FIG. 8 is a flow chart of a method of operating and/or assembling an anaerobic digestion system according to some embodiments.

Referring now to FIG. 8, a process 800 for assembling an anaerobic digestion system is provided according to some embodiments. This could be used, for instance, with system 100 of FIGS. 1A and 1B. In step 802, the process may begin with placing a cover over an anaerobic digester cover (e.g., lagoon). In step 804, one or more weights are placed on the cover to form one or more pleated features (e.g., corners). In step 806, which may be optional in some embodiments, the weights are filled (e.g., with water or gravel). In step 808, which may be optional in some embodiments, one or more additional systems are implemented. This could include, for instance, assembling, attaching, and/or operating a thermal management system, gas level sensing system, and/or water recovery system that uses at least one of the weights. An energy storage and recovery system may also be incorporated at step 808. Depending on the type of biomass storage container, the process 800 may also include digging and preparing (e.g., applying one or more liners or claddings) the container. According to embodiments, process 800 may further include one or more of the steps described with respect to FIGS. 2A and 3B.

Figure 9:
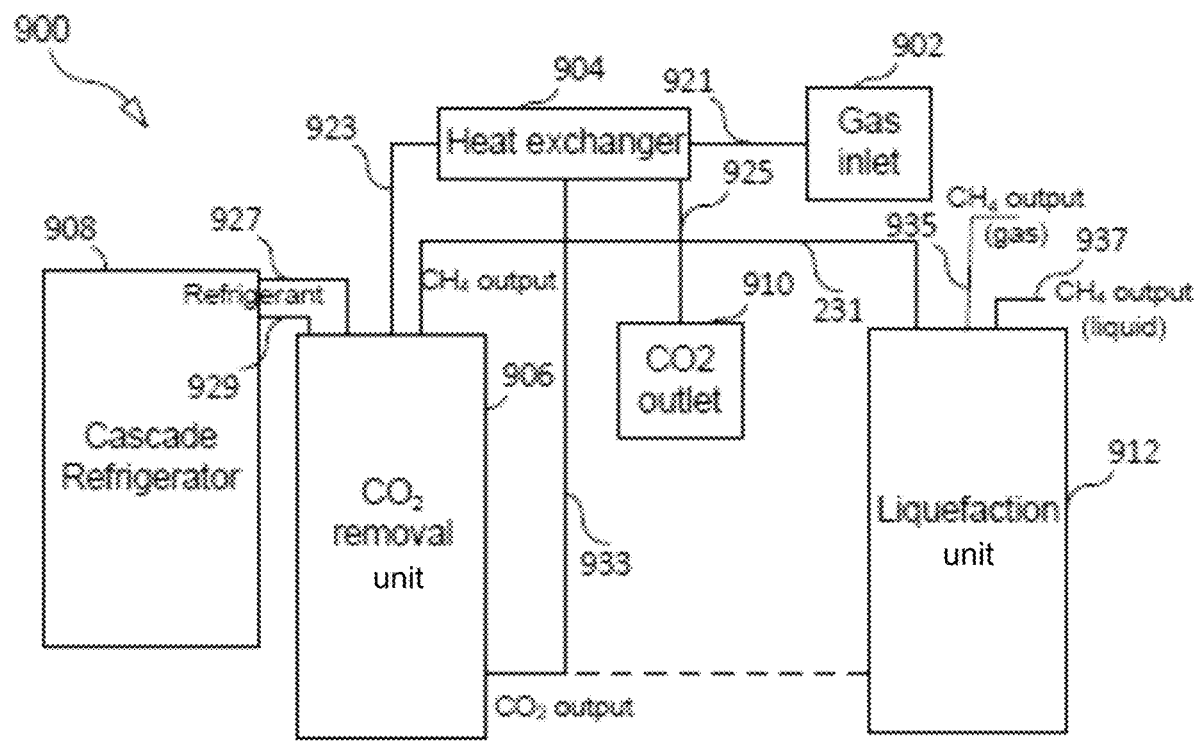
FIG. 9 illustrates an exemplary biogas separation and methane liquefier according to some embodiments.
Figure 9A:
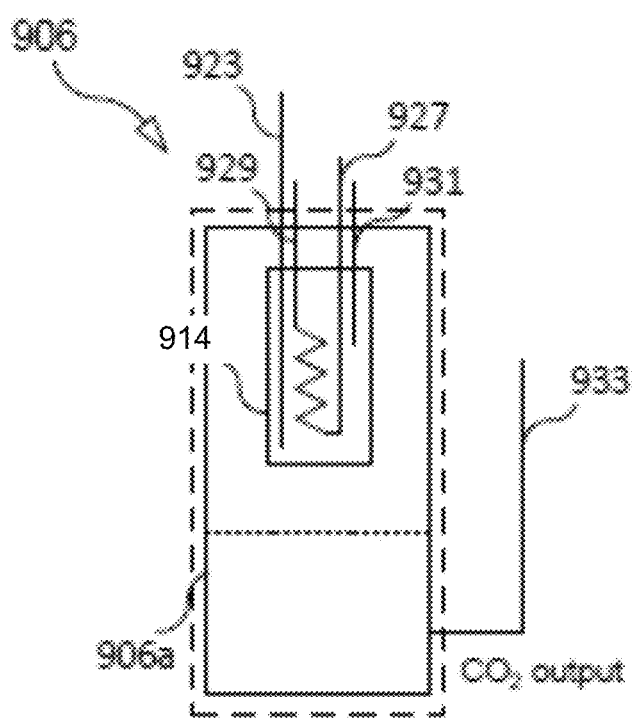
FIG. 9A illustrates an exemplary $CO_2$ removal unit (e.g., cold box) according to some embodiments.
Figure 9B:
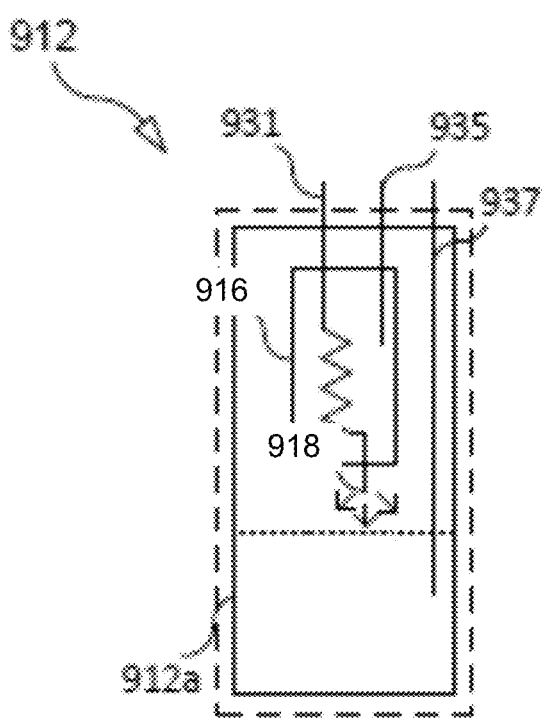
FIG. 9B illustrates an exemplary liquefaction unit (e.g., Joule-Thompson unit) according to some embodiments.
Figure 9C:
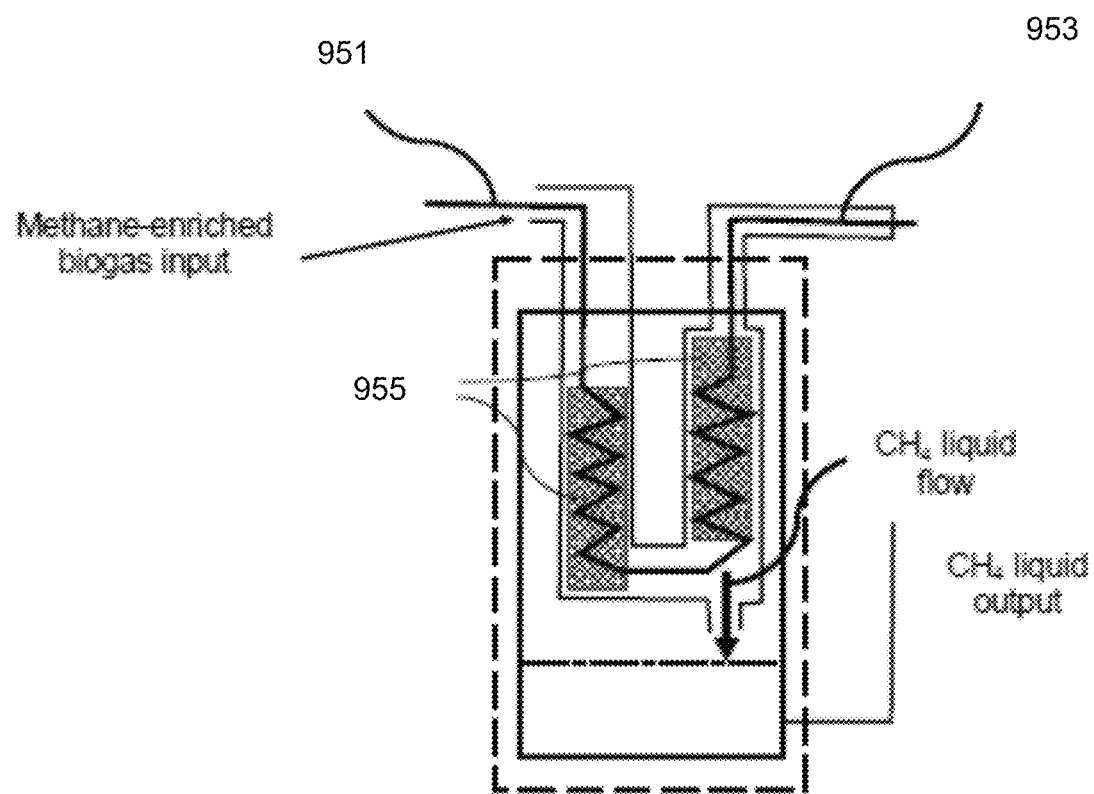
FIG. 9C illustrates an exemplary combination $CO_2$ removal and liquefaction unit according to some embodiments.

FIG. 9 illustrates an exemplary biogas separation and methane liquefier 900 for use with one or more embodiments. FIG. 9A illustrates an exemplary $CO_2$ removal unit (e.g., cold box) 906 according to some embodiments. FIG. 9B illustrates an exemplary liquefaction unit (e.g., Joule-Thompson unit) 912 according to some embodiments. FIG. 9C illustrates an exemplary $CO_2$ removal and liquefaction unit according to some embodiments. The biogas separation and methane liquefier 900 is now described with reference to FIGS. 9, 9A, 9B, and 9C.

The biogas mixture (e.g. the methane enriched biogas, such as from one or more of the methane-enriched spaces of the anaerobic digestion system 100) is optionally first compressed by a compressor (not shown) to a processing pressure (e.g. between 100 bar and 300 bar), filtered by one or more filters (not shown), and then fed to the gas inlet 902. As a general matter, the lower the processing pressure, the less energy is required for liquefaction, while the higher the processing pressure, the easier it is to separate the carbon dioxide and methane (e.g. because there is more separation in phase diagrams for allowing the carbon dioxide to become a liquid while the methane remains a gas). In embodiments, the processing pressure could be as low as 30 bar, and may be higher than 300 bar. Also, the size of components may generally be made smaller as the pressure increases, e.g. due to the volume of gas decreasing at higher pressure. As noted, in exemplary embodiments, the processing pressure is around 100 bar to 300 bar. The biogas entering at inlet 902 will be, in some embodiments, approximately 85% methane and approximately 15% carbon dioxide, from about 100 bar to 300 bar, and about 20° C. (or whatever temperature the biogas is at after exiting the anaerobic digestion system 100). In embodiments, the biogas may be pre-processed, such that one or more of compression and/or filtering are not required.

From gas inlet 902, the biogas mixture passes through piping 921 to a heat exchanger 904 and then through piping 923 to a $CO_2$ removal unit (e.g., cold box) 906. Heat exchanger 904 may, in some embodiments, be cooled by $CO_2$ (e.g. at around −60° C.) before the biogas flows through piping 923 to enter the $CO_2$ removal unit (e.g., cold box) 906. The $CO_2$ (e.g., in liquid form) that cools the heat exchanger 904 may be supplied by the $CO_2$ removal unit 906 by piping 933 (in which case it will be at approximately the temperature of the cold box), prior to the liquid $CO_2$ exiting the system by piping 925 to the $CO_2$ outlet 910. Such $CO_2$ can also be provided to the liquefaction unit 912 in some instances, as a source of cold.

Inside the $CO_2$ removal unit 906, there may be a second heat exchanger 914 (see, e.g., FIG. 9A), which may be cooled by a high power cascade refrigerator 908 driving a circuit of cooled refrigerant (or other cooling method, e.g. a cryocooler or liquid cryogen). The cooling by the cascade refrigerator may cool the $CO_2$ removal unit (e.g., cold box) 906 to a temperature appropriate for causing the carbon dioxide to liquefy (or drop out as a solid) while maintaining the methane as a gas. The precise temperature will depend on the processing pressure. For instance, at pressures of about 100 bar-300 bar and temperatures of about −40° C. to −60° C., methane is a gas and $CO_2$ condenses to form liquid. In embodiments, the temperature that the $CO_2$ removal unit (e.g., cold box) 906 is cooled to may be approximately from about −40° C. to −60° C., and in embodiments may be approximately −60 C°. Refrigerator 908 is coupled to the $CO_2$ removal unit (e.g., cold box) 906 by piping 927 and 929, which carries refrigerant into and out of the $CO_2$ removal unit (e.g., cold box) 906, respectively.

According to embodiments, the methane is cooled but remains a gas as it passes over the heat exchanger 914, whereas the $CO_2$ condenses to a liquid (or, in some embodiments, a solid) and falls to the bottom 906a of the $CO_2$ removal unit (e.g., cold box) 906. The extracted $CO_2$ may then exit $CO_2$ removal unit (e.g., cold box) 906 by piping 933. In some embodiments, solid $CO_2$ may be retained in solid form until a batch of biomethane has been refined or the box is full, when the system may be shut down, the equipment warmed, and the $CO_2$ may be removed in either gaseous or liquid form. As noted above, it may in some embodiments first pass through the heat exchanger 904 in order to take advantage of the fact that liquid $CO_2$ is cooled by the cold box (e.g., to approximately −60° C.). Doing this can save considerable energy requirements, because the cascade refrigerator 908 will not need to cool the gas entering the cold box as much in such a case. When the $CO_2$ leaves the heat exchanger 904 by piping 925 and reaches the outlet 910, it may have an approximate temperature of around 20° C. (or approximately whatever temperature the biogas entering the heat exchanger 904 has), and be at about 100 bar-300 bar. The $CO_2$ removal unit (e.g., cold box) 906 is insulated (insulation shown by dashed lines around $CO_2$ removal unit (e.g., cold box) 906) to conserve cold and reduce the cooling power requirement.

The now cold, but still pressurized methane, passes by piping 931 to the liquefaction unit (e.g., Joule-Thompson unit) 912. The liquefaction unit may also serve as a storage unit. However, the system 900 may include additional methane storage units (not illustrated), which can be removable as needed. When passing through piping 931, the gas is approximately 99% pure methane, with around 1% carbon dioxide, is still at around 100 bar-300 bar, and is cooled due to the $CO_2$ removal unit (e.g., cold box) 906 (e.g. to approximately −60° C.). In the examples of FIG. 9B, the Joule-Thompson unit 912 is where the liquefaction stage of the process for the methane gas takes place. The unit 912 is insulated (shown in dashed lines), which can help conserve cold and reduce the cooling power requirement. The pressurized methane passes through a heat exchanger 916 (see FIG. 9B) within unit 912. The heat exchanger 916 may be cooled by the outgoing low pressure methane (that passes through piping 935), causing the pressurized methane to cool further before passing through an orifice 918 (such as a Joule-Thompson orifice), where the methane finally cools to a low enough temperature to liquefy. The methane entering through piping 931 is at about the pressure of the methane in the $CO_2$ removal unit (e.g., cold box) 906, e.g. approximately 100 bar to 300 bar in some embodiments. The pressure as the gas passes through the orifice 918 reduces to a low pressure, e.g. about 1 bar. The methane is cooled by the heat exchanger 916 to a temperature at which the methane will liquefy. This will depend on the pressure after the gas passes through the orifice 918, but in some embodiments, the temperature may be approximately −161° C. or lower. If the temperature is too cold, the methane may solidify, which would block the output pipework 957. Therefore the temperature is preferably cold enough to cause the methane to become liquid, but not too cold to solidify the methane. The liquefied methane falls to the bottom 912a of the unit 912, where it is at an approximate temperature in some embodiments of about −161° C. Because the methane is already cold and is at high pressure when it enters unit 912, the liquefaction fraction will be high, typically 70%-80%, resulting in a very efficient process. That is, most of the methane will liquefy and exit by piping 937 as liquid methane, for instance at retrieval or when moved to on-board storage. Some of the methane, however, will remain in gaseous form, and will exit via piping 935 as gas, at a lower pressure of about 1 bar. At this point, both the liquid and gaseous methane may be very pure, in embodiments more than 99% pure methane.

The Joule-Thompson unit 912 just described is an exemplary mechanism for liquefying methane gas. In some embodiments, a cryocooler, Brayton cycle device, or other device for liquefying methane may be used. Further, while the description above noted that the cold box is configured to liquefy $CO_2$ gas but not methane gas, in embodiments the cold box may be configured to liquefy and/or solidify $CO_2$ gas but not methane gas.

For high levels of methane refinement where the $CO_2$ makes up a small fraction of the total volume (such as approximately 1-10%), the $CO_2$ can conveniently be removed as a solid without requiring equipment (such as a cold box or heat exchanger) that is bulky or too large for being used as part of a mobile biogas processing plant. The methane can then be simultaneously removed as a liquid at low pressure. By sizing the heat exchanger appropriately, this can occur within a common liquefaction and low-pressure $CO_2$ removal unit (e.g., cold box enclosure), such as shown in FIG. 9C. In certain scenarios where there is limited power availability at the site to drive a compressor, this can provide a more energy-efficient solution and can be further enhanced through the use of a low-cost sacrificial cold source such as an inert liquid cryogen, for example liquid nitrogen. Where appropriate this can conveniently be brought to the site as a liquid in sufficient quantity to carry out the gas processing required for the period in question. In some embodiments, gas inlet 902 is adapted for receiving $CO_2$ enriched biogas. In embodiments, the methane-enriched and $CO_2$ enriched inlets comprise a single inlet 902.

As well as the source of cold being a sacrificial cryogenic liquid, where convenient it could also be a mechanical cooler used to liquefy air at the site or alternatively a close cycle refrigeration circuit. Whichever source is used, it should provide sufficient cooling for both phase changes in the $CO_2$ gas to solid and the methane gas to liquid in embodiments. Where the refrigerant is a sacrificial cryogenic liquid such as liquid nitrogen or liquid argon that has a boiling point lower than the freezing point of methane care must be taken to ensure that the methane liquefaction process temperature is maintained above the freezing point of methane at the process operating pressure otherwise solid methane will form causing blockages in the heat exchanger path. At atmospheric pressure methane freezes at approximately $-182°$ C. which is above both the boiling point of liquid nitrogen and liquid argon. A safe liquefaction operation temperature can conveniently be achieved by holding the sacrificial cryogenic liquid at a higher than atmospheric pressure via a pressure release valve. This also has the advantage of providing a failsafe system ensuring that its boiling point is maintained above that of the freezing point of methane without the need for active control. For liquid nitrogen for example a pressure of 5 bar would maintain a boiling point of approximately $172°$ C. ensuring that the methane gas stream never freezes.

According to embodiments, solid $CO_2$ may be used to improve the liquefaction process in stage 912. For instance, a refrigerant liquid can be introduced to cause solid-form $CO_2$ buildup in stage 912, which can in turn provide a source of cold for liquefaction of the methane. As such, a liquefaction stage 912 may comprise a refrigerant liquid input and output, as shown in FIG. 9C. In some embodiments, liquid refrigerant may be provided in an outer region of the stage 912, which is separate from the liquefaction chamber, as illustrated with the dashed-line box of FIG. 9C. In embodiments, the dashed-line box may instead represent an insulation layer. In some embodiments, and as illustrated in FIG. 9C, a sacrificial refrigerant liquid (e.g., liquid nitrogen or liquid air) can be introduced by a flexible tube or pipe 951. Similarly, it may be extracted (e.g., in gas form) via an outlet tube or pipe 953. In some embodiments, and as shown in FIG. 9C, the refrigerant tube or pipe may be located within the input tube or pipe of the biogas (e.g., methane-enriched biogas). That is, the liquefaction stage may use a tube-in-tube (or pipe-in-pipe, or tube-in-pipe) arrangement with cold liquid flowing within the biogas flow path (or vice-versa). This arrangement may beneficially cause a build-up of solid $CO_2$ 955 in the path of the biogas, which can have benefits for both purification and cooling of the biogas. That is, biogas may flow through solid or liquid-form $CO_2$ extracted from biogas or generated from a sacrificial source.

One or more embodiments are further described below.

In a first example, an anaerobic digester (or anaerobic digestion system) is provided that comprises: a biomass storage container (e.g., a slurry lagoon with one or more tapered sidewall); and a cover (e.g., a gas membrane) positioned over the biomass storage container, wherein the cover is sealed at an outer edge of the anaerobic digester to form a water (e.g., rainwater) collection region. The digester may further comprise an angled bracket (e.g., a gutter ring beam), wherein the bracket is configured to confine the water in the water collection region. The digester may further comprise an installation post (e.g., comprising a post, insulation, and cladding). In certain aspect, the biomass storage container comprises a lagoon liner membrane. The digester of this example may further comprise one or more membranes (e.g., a slurry cover membrane) between the biomass storage container and the cover. At least one of the membranes is selectively permeable between methane and $CO_2$, or at least one of the membranes is non-permeable to biogas and its constituent materials. In this example, the cover, bracket, slurry cover membrane, and lagoon liner membrane may all be attached to the installation post. Additionally, at least one of the cover, bracket, slurry cover membrane, and lagoon liner membrane is attached to the installation post with one or more clamps (e.g., an outer membrane clamp and inner membrane clamp). This assembly may further comprise a gasket (e.g., a PVC closed cell foam gasket) on a top surface of the installation post and below one or more of the cover, bracket, slurry cover membrane, and lagoon liner membrane. In certain aspects, the cover is configured for protecting the biomass storage container and its contents against rain and wind. In certain aspects of the example, the cover is transparent and is configured to provide solar heating for the anaerobic digester. The cover may be made of a fabric reinforced polymer material (e.g., comprising a plurality of sheets). A gas filtrations system may also be included, wherein the gas filtration system is configured to process sour gas extracted from the biomass storage container and provide refined biogas to a region between the one or more membranes (e.g., slurry cover membrane) and the cover. In certain aspects, the processing of sour gas comprises removal of one or more of hydrogen sulfide and $CO_2$. Other systems and features may be included, such as: a thermal management system (e.g., as described with respect to Example 2); a gas or slurry state monitoring system (e.g., as described with respect to Example 3); an energy recovery system (e.g., as described with respect to Example 4); and/or one or more cover weights (e.g., as described with respect to Example 5). In some embodiments, the cover has a rectangular or square shape and comprises one or more pleated corners. Another system that may be used in Example 1 is a water recovery and re-use system, wherein the water recovery and re-use system is configured to divert water from the water collection region to a second system (e.g., a water storage tank, washing station, livestock watering system, irrigation system). The water recovery and re-use system may comprise a water cleaning stage interposed between the collection region and the second system. In some instance, the digester may also comprise a mixer for circulating slurry within the biomass storage container, for instance, using an input/output pipe and one or more angled mixing outlets (e.g., angled to match the angel of one or more of biomass storage container sidewalls). The digester may also have a pump, wherein the pump is configured to move water from the cover to the water collection region (or vice-versa). In some embodiments, the cover, bracket, slurry cover membrane, and lagoon liner membrane are arranged such that biogas generated in the anaerobic digester does not come in contact with metallic components (e.g., to prevent corrosion). Additionally, the water collection region can cover all gas seals at the installation post, such that a gas leak would be identifiable by monitoring the water collection region.

According to embodiments, a method is provided for operating a digester according to Example 1. The method may comprise one or more of the following steps: (i) providing a slurry or other bio-materials to the container, such as pumping slurry to a covered lagoon; (ii) operating or otherwise controlling the anaerobic digestion process within the digester (e.g., temperature control, mixing, venting); (iii) extracting and/or processing gas from the digester; (iii) monitoring a water collection region for gas leaks; (iv) operating an associated thermal management system (e.g., flowing warm water between the cover and the slurry region to either provide heat to the digestion process or melty ice/snow on the cover), for instance, based on feedback from one or more level or temperature sensors (e.g., as described in Example 3); (v) operating a water management system; and (vi) performing energy storage or recovery.

In a second example, a thermal management system for an anaerobic digester is provided. The system comprises: a circulation device (e.g., comprising one or more pumps); and a plurality of tubes (or pipes) connected to the circulation device, wherein the plurality of tubes comprise: (1) one or more tubes on a surface of an anaerobic digester cover; and/or (2) or one or more tubes on a surface of (e.g., on a surface of a liner of) or within a biomass storage container of the anaerobic digester. The plurality of tubes may be water-filled. In this example, the circulation device is configured to flow warm water from the surface of the anaerobic digester cover to the biomass storage container (e.g., to improve an anaerobic digestion process in the container), and/or flow warm water from the biomass storage container surface of the anaerobic digester to the cover (e.g., to melt snow on the cover, which can cause damage to the digester and/or its components). In certain aspects, at least one of the tubes on the surface of digester cover is a weighted tube arranged to keep the cover in place (e.g., as described with respect to Examples 1, 3, and 5). In this example, the biomass storage container may comprise a thermal storage region (e.g., filled with pea gravel), where the system is configured to flow warm water to the thermal storage region.

According to embodiments, a method of operating the thermal management system of Example 2 is provided. The method may comprise the steps of pumping heated water through the weight tubes to remove ice on the over and/or recovering heat from the outer cover and pumping this heat into the slurry, thereby increasing the digestion rate. One or more thermal management operations may be based on a determination of a status of the digester (e.g., based on a sensor output as described in Example 3).

In a third example, an anaerobic digester (or anaerobic digestion system) is provided that comprises: a biomass storage container (e.g., a slurry lagoon); a cover (e.g., a gas or slurry membrane) positioned over the biomass storage container; and one or more sensors configured to indicate a gas or slurry state (e.g., level) of the anaerobic digester. The anaerobic digester may further comprise a cover weight, where at least one of the sensors is a pressure sensor attached to (e.g., within) the weight. In some embodiments, at least one of the sensors is a line-of-sight sensor (e.g., a camera) configured to monitor a top level of the cover. In some embodiments, at least one of the sensors is an angular sensor array on the cover (e.g., a festoon string of gyroscopic sensors). In this example, the digester may also include a processing circuit (e.g., a processor, memory, and transmitter) configured to determine and report (e.g., locally, over a wireless channel, using the Internet, etc.) the gas or slurry state based on measurements form the one or more sensors.

According to embodiments, a method of operating the anaerobic digester of Example 3 is provided. The method may include, for instance, monitoring the amount of fugitive methane in the bag, which is required for remote control of monitoring of the lagoon and associated gas recovery plant. Additionally, one or more systems may be operated responsive to the sensing. This could include, for instance, activation of a thermal system, starting/stopping a slurry mixing process (e.g., to adjust the level of the gas up or down or otherwise affect digestion rate); venting (e.g., if the gas level or pressure is too high); or initiating gas processing (e.g., if the level reaches a predetermined volume or pressure threshold).

In a fourth example, an energy storage system is provided. The system comprises: one more storage containers of gaseous or liquid materials (e.g., compressed gas or cryogenic liquid); a gas pressure driven electrical generator (e.g., a turbine) coupled to the one or more storage containers and configured to generate power (e.g., electricity) using gas generated (e.g., vented) from the one or more storage containers; and a gas buffer configured to store at least a portion of an exhaust gas after it is used by (e.g., passes through) the generator. The gas or liquid could be, for instance, methane, $CO_2$, hydrogen, or a mixture thereof. In certain aspects, the gas buffer is a part of an anaerobic digester (e.g., as described with respect to Examples 1, 3, and 5). For instance, the gas buffer can be the region located between a slurry region and a cover of the anaerobic digester. In certain aspects, a gas processing system (e.g., comprising a compressor, dryer, cooler, liquefaction stage, liquid storage vessel) can be included and configured to extract the gas from the gas buffer and store it in the one or more storage containers. In some embodiments, wherein the energy storage system is part of a mixed electricity generating system comprising one or more of photovoltaics and wind energy devices (e.g., a windmill), and/or an internal combustion (IC) engine is configured to operate using the gas (e.g., after expansion). While an internal combustion engine is used as an example, other engines (such as other combustion engines, or non-combustion engines) may be used as well in this example and other embodiments.

According to embodiments, a method of operating an energy storage system according to Example 4 is provided. For instance, an energy recovery process may be performed that comprises: venting gas from one more storage containers of gaseous or liquid materials (e.g., compressed gas or cryogenic liquid); generating electricity using the vented gas; and passing remaining vented gas to a gas buffer. Generating electricity may comprise operating a turbine using the vented gas. Other types of power or mechanical energy may be generated according to embodiments. In certain aspects, the method may also comprise storing gas from the gas buffer in the one or more storage containers, for instance, by compressing the gas from the gas buffer, wherein the gas from the buffer was previously used to generate electricity in the generating step. In embodiments, at least one of the venting gas and storing gas is based at least in part on the supply of electricity from a photovoltaic, wind energy device, or battery, and/or energy used for the storing step is provided by a photovoltaic, wind energy device, or battery. In embodiments, passing the remaining vented gas to a gas buffer comprises passing the remaining vented gas to an anaerobic digester (e.g., as described with respect to Example 1). The method of this example may also comprise passing the generated electricity to a mains electricity system. The method of this example may also comprise passing the vented gas through a heating element before the electricity generation step. In some embodiments, the method comprises: before the venting step, generating gas in an anaerobic digester; and storing it in the one or more storage containers, wherein the step of passing the remaining vented gas to a gas buffer comprises passing the remaining vented gas to the anaerobic digester used to generate the gas. Embodiments may comprise using the vented gas to power an engine (e.g., after an expansion of the gas that utilizes waste heat).

In a fifth example, an anaerobic digester is provided that comprises: a biomass storage container; a cover positioned over the biomass storage container; and one or more weights, wherein at least one of the weights is positioned on a top surface of the cover. In some embodiments, the cover is rectangular or square and at least one of the weights forms a pleated corner of the cover. In some embodiments, a weight is arranged in each corner of the cover. A weight may also be arranged in a center region of the cover or on a slurry membrane of the biomass storage container. In certain aspects, at least one of the weights comprises a pressure sensor. In certain aspects, at least one of the weights is a tube (or pipe). In embodiments, at least one of the weights is a hollow tube, a solid tube, a rock-filled tube, or a water-filled tube. In certain aspects, the weight tube is connected to a water collection region of the anaerobic digester and configured to move water from the cover to the collection region (or vice-versa). In certain aspects, the weight tube is connected to a water circulation device. In certain aspects, the weight tube is filled with gravel or heated water. In certain aspects, the one or more weights are arranged to create tension on cover and prevent flapping of the cover in the wind. The cover may be expandable upon an increase in gas generated in the biomass storage container (e.g., expansion via one or more pleats).

According to embodiments, a method of assembling the anaerobic digester of Example 5 is provided. The method may comprise, for instance, the steps of placing the cover, placing the weights to form pleated corners, assembling/attaching any thermal management system, and optionally filling one or more weights. A similar method may be used to assemble the digester of Example 1, for instance.

While one or more of the examples provided herein are described with respect to an anaerobic digester, according to embodiments, the individual components and systems may be implemented separately from the digesters described in the embodiments of this disclosure.

Lagoon Cover

FIGS. 10A and 10B show typical open slurry systems 1000. The slurry lagoons may have an irregular shape. When a slurry lagoon is "open," i.e. not covered, then biogas (such as methane) can escape from the lagoon as a consequence. This can be environmentally harmful. Also, the lagoon is exposed to the elements, including precipitation such as rainwater and snow. Over time, this precipitation may account for a significant fraction of the volume of the slurry. This can result in a need for larger slurry lagoons to account for the precipitation that will also be stored.

Embodiments herein described refer to a cover for a lagoon. The cover can be used in a covered slurry lagoon system having a slurry lagoon and a cover for the slurry lagoon. Embodiments also refer to the covered slurry lagoon system. In embodiments, the cover for a lagoon can be used in existing open slurry lagoons, to convert such open slurry lagoons into a covered slurry lagoon system.

FIG. 11 is a cross-sectional schematic illustrating a covered slurry lagoon system 1100 according to an embodiment. The covered slurry lagoon system 1100 includes a slurry lagoon 1102 having a bottom wall 1104 and side walls (or banks) 1106. The covered slurry lagoon system 1100 also includes a cover 1108. The cover 1108 may be an expandable membrane having a plurality of sections 1110. In embodiments, the sections 1110 may expand differently from each other, e.g. some may stretch out more and some may stretch out less than others. The sections 1110 may be in a single row, or may include a number of different rows such that there is a matrix like pattern of sections 1110. Where two sections 1110 come together (shown at points 1111 and 1113), a rope 1112 and an elastic material 1114 are coupled to the cover 1108, extending between and attached to the points 1111 and 1113. The rope 1112 acts to limit expansion of the cover 1100. As gas fills the membrane and points 1111 and 1113 tend to be expanded, the rope 1112 becomes taut and prevents further expansion. The elastic material 1114 acts to compress the cover 1100. The elastic material 1114 pulls between points 1111 and 1113 and helps provide shape to the cover 1100. In embodiments, the elastic material 1114 is a string of elastic, or a tubular elastic component, that extends between points 1111 and 1113 and compresses the membrane.

In embodiments, rope 1112 may be replaced with any restraining member that can limit or control the expansion of the expandable membrane. The restraining member may be coupled to the expandable membrane and configured to limit expansion of the expandable membrane, for example, in a similar manner to the rope 1112. In embodiments, elastic material 1114 may be replaced with any stretchable member (e.g., as shown in FIGS. 21A and 21B) that can compress the expandable membrane. The stretchable member may be coupled to the expandable membrane and configured to compress the expandable membrane, for example, in a similar manner to the elastic material 1114.

The covered slurry lagoon system 1100 also includes a skirt 1116 that surrounds the outer perimeter of the cover 1108. The skirt may be weighted so that it remains submerged within the slurry lagoon 1102. The covered slurry lagoon system 1100 also includes one or more gas inlets and gas outlets. For example, a gas outlet takes raw gas out of the slurry lagoon 1102 via piping 1118, e.g. through a valve in the skirt 1116, and allows the raw gas to be fed into gas processing system 1122. The processed gas can then be fed back into cover 1108 by a gas inlet via piping 1120, e.g. through a valve in the cover 1108. In this way, the cover 1108 acts as a storage for processed gas from the slurry lagoon 1102. In embodiments, different types of gas (e.g., different purifications of carbon dioxide or methane) may be stored separately in cover 1108. For example, gas permeable/semi-permeable membranes (such as those disclosed in the "Anaerobic Digestion" section) may be used within cover 1108 to provide for different storage areas. In such cases, the membrane may be chosen so that the heavier gasses may be at the lower layers, and the lighter gasses may be allowed to rise through the permeable membranes, to appropriately segregate the different types of gas. Similarly, gas impermeable membranes may also be used within cover 1108 to provide for different storage areas. In such cases, gas processing system 1122 will have separate gas outlets for the different types of gasses that can then be directed to the appropriate storage areas. A gas processing system 1122 may include the gas processing systems disclosed in the "Anaerobic Digestion" section.

The cover 1108 effectively acts as a storage space for gas. A mobile processing station may be used (such as those disclosed in the "Anaerobic Digestion" section) for recovering the gas that is stored in the cover 1108. The cover 1108 may also provide thermal insulation, such as disclosed in the "Anaerobic Digestion" section, and thermal management, water collection and re-use, and/or energy recovery systems, such as disclosed in the "Anaerobic Digestion" section, may also be used with the covered slurry lagoon system.

The cover 1108 may be made from a number of different materials, including one or more of polypropylene, polyethylene, polyether ether ketone (PEEK), polyvinyl chloride (PVC), polytetrafluoroethylene (PTFE), polyphenylene sulfide (PPS), and ethylene tetrafluoroethylene (ETFE). Exemplary trade-named materials include an XR-5 geo-membrane and Sattler Pro-tex Polyplan composite.

As shown in FIG. 11, the cover 1108 is empty, meaning that it does not yet have any biogas from the slurry lagoon 1102 in it. In this case, the cover 1108 is in an unexpanded state. The right-most segment 1110 shown in FIG. 11 has a height h1 in this unexpanded state. As shown in FIG. 12, the cover 1108 is full, meaning that it has reached its capacity of storing biogas from the slurry lagoon 1102. In this case, the cover 1108 is in an expanded state. The right-most segment 1110 shown in FIG. 12 has a height h2 in this expanded state. The height h2 is larger than h1, and the difference between h2 and h1 represents an amount of expandability for the cover 1108. The amount of expandability may be controlled by the length of the rope 1112 in this embodiment. As will be explained, the expandability of different sections 1110 may vary in some embodiments. The amount of storage capacity of cover 1108 is proportional to the expandability of the different sections 1110.

As shown in FIG. 12, the end-most sections 1110 have rope 1112 and elastic material 1114 at the outer edges also, not just in the interior where two or more sections 1110 meet. In embodiments where this is the case, the outer edges of the expandable membrane are allowed to move as the amount of gas in storage empties and to pull in as the amount of gas in storage fills. The overall width and length of the membrane may drop to the position of the outermost elastic material 1114 and rope 1112 when the storage space is full.

FIG. 13 is a cross-sectional schematic illustrating a covered slurry lagoon system 1300 according to an embodiment. As shown, only half of the slurry lagoon system 1300 is illustrated, with the remainder being symmetric. Slurry lagoon system 1300 is similar to slurry lagoon system 1100, and like reference numbers indicate identical or functionally similar elements. This embodiment illustrates a water collection area 1302, which allows rainwater to collect at the area 1302 and then exit the system by piping 1304. In some embodiments a pump may be used to cause the water to exit the system, while other embodiments may rely on gravity. In the configuration shown, gravity may direct rainwater from water collection area 1302 through the piping 1304 and out of the slurry lagoon system 1300. The rainwater leaving the slurry lagoon system 1300 may be collected and used. The sloping contour of the cover 1108 allows the rainwater to collect in water collection area 1302. As illustrated, each section 1110 may have a different height, e.g., d1, d2, d3, and d4, each shown monotonically decreasing. Similarly, the heights of sections 1110 for the sections not illustrated may be symmetrical to those that are illustrated, such that the water collection area 1302 is roughly in the center of the cover 1108. The cover 1108 may be designed so that the water collection area 1302 is in another location, e.g., depending on the needs of a particular slurry lagoon 1102 and the surrounding environment.

As shown, there is a gap 1306 between the skirt 1116 and the side wall (or bank) 1106. In this case, the side wall 1106 is slanted, and slopes inward toward the slurry lagoon 1102. In this embodiment, the perimeter of the cover 1108 aligns with the bottom wall 1104 of the slurry lagoon 1102, as indicated by the dashed line e in FIG. 13. The gap 1106 permits water 1308 to collect in this region. The collection of water 1308 in this region of gap 1106 can have the benefit of covering one or more gas seals, such as the seals where cover 1102, skirt 1116, and/or a liner are connected. When filled with water 1308, monitoring and detection of leaks in the seals are possible. For example, if gas were to escape the seals, it would form bubbles in the water 1308 that would be visibly or audibly detectable. For example, piping 1118 may be connected to a gas inlet in the skirt 216, where the gas inlet includes a valve that can be covered by the water 1308 in the region of gap 206.

FIG. 14A is a top view and FIG. 14B is a sectional schematic illustrating a rigid body 1400 according to an embodiment. As shown, rigid body 1400 includes tubing (e.g., pressurized tubing) that forms an outer perimeter 1402 with an inner support structure 1404. Tubes such as those disclosed in the "Anaerobic Digestion" section may also be used here. In some embodiments, the skirt 1116 may be comprised in whole or in part from rigid body 1400. Although the perimeter is a square in top view, the shape of the perimeter 1404, as well as the inner support structure 1404, may vary e.g. according to the design of a particular slurry lagoon 1102 and surrounding environment.

FIG. 15 is a cross-sectional schematic illustrating a covered slurry lagoon system 1500 according to an embodiment. As shown, only part of the slurry lagoon system 1500 is illustrated, with the line 1502 indicating that the slurry lagoon system 1500 would continue out further. Slurry lagoon system 1500 is similar to slurry lagoon systems 1100 and 1300, and like reference numbers indicate identical or functionally similar elements. As shown, there is a solid edge ring 1504. This may be a concrete barrier, for example, that surrounds the slurry lagoon 1500 and forms an outer perimeter. A lining 1506 may be used, which connects to the skirt 1116, and limits the area of gap 1306 where water 1308 may accumulate. The lining 1506 may be connected to the solid edge ring 1504 also.

FIG. 16 is a cross-sectional schematic illustrating a covered slurry lagoon system 1600 according to an embodiment. As shown, only part of the slurry lagoon system 1600 is illustrated, with the line 1602 indicating that the slurry lagoon system 1600 would continue out further. Slurry lagoon system 1600 is similar to slurry lagoon systems 1100, 1300, and 1500, and like reference numbers indicate identical or functionally similar elements. As shown, sections 1110 are configured to create a dished upper surface on an exterior of the cover 1108. For example, each section 1110 may have a different height (shown as d1 through d8), e.g. so that rainwater may collect at a common area. In some embodiments, the shortest section 1110 (shown here with height d6) may be approximately in the middle of the cover 1108, with sections 1110 on either side the shortest section 1110 getting progressively taller as they move away from the shortest section 1110. The height of a given section 1110 may be configured based on the rope 1112 and elastic material 1114. For example, from the outside going toward the shortest section 1110, the elastic material 1114 may start out weak and the rope 1112 may be long while moving inward the elastic material 1114 progressively gets stronger and the rope 1114 progressively gets shorter. In this way a dished upper surface can be created that causes rainwater to collect at a designated collection area.

FIG. 17 is a cross-sectional schematic illustrating a covered slurry lagoon system 1700 according to an embodiment. As shown, only part of the slurry lagoon system 1700 is illustrated, with the line 1702 indicating that the slurry lagoon system 800 would continue out further. Slurry lagoon system 1700 is similar to slurry lagoon systems 1100, 1300, 1500, and 1600, and like reference numbers indicate identical or functionally similar elements. As shown, rainwater may collect at water collection area 1302, and then exit the system by piping 1304 via a water outlet 1704. Water outlet 1704 may facilitate redirecting the rainwater to other uses.

FIG. 18 is a cross-sectional schematic illustrating a covered slurry lagoon system 1800 according to an embodiment. Slurry lagoon system 1800 is similar to slurry lagoon systems 1100, 1300, 1500, 1600, and 1700, and like reference numbers indicate identical or functionally similar elements. As shown, rainwater may collect at water collection area 1302, and then exit the system by piping 1802. In this embodiment, the piping 1802 does not rely on gravity, and instead the water in water collection area 1302 must be pumped out by a water pump through piping 1802.

FIG. 19 is a cross-sectional schematic illustrating a covered slurry lagoon system 1900 according to an embodiment. Slurry lagoon system 1900 is similar to slurry lagoon systems 1100, 1300, 1500, 1600, 1700, and 1800, and like reference numbers indicate identical or functionally similar elements.

FIGS. 20A and 20B illustrate a schematic perspective rendering of a slurry lagoon system as described herein. For example, strings of elastic material 1114 are visible in the rendering shown in FIGS. 20A and 20B, extending in a grid-like pattern where two or more sections 1110 meet.

FIGS. 21A and 21B illustrate a clock spring with a rotary pulley system according to an embodiment. In some embodiments, elastic material 1114 may be replaced with any stretchable member, such as, for example, spring or a spring and pulley system. For example, a clock spring may provide an increased expansion capability over an elastic polymer expanding tether. Elastic polymers are fundamentally limited by their coefficient of elasticity, which is a material property. Typical elastomers such as silicone rubber have a stretch capability of 3-4 from their at rest length before they are permanently damaged and therefore extended. This limits the maximum height that the cover 1108, acting as a gas storage, can be held under tension compared with the lowest height. However, a clock spring held with a rotary pulley system (such as shown in FIGS. 21A and 21B) can provide much higher ratios between the fully extended state and the fully home state. For example, a rotary steel tape measure can easily achieve linear expansion factors of 20:1.

Accordingly, when using a spring or a spring and pulley system like this, very large quantities of biogas can be held within the storage bag relative to the empty state, while still maintaining sufficient tension between the top and bottom of the cover 1108 to ensure stability in high wind and rain conditions. In addition, the level of tension can be readily tuned by the selection of the spring strength.

While various embodiments of the present disclosure are described herein, it should be understood that they have been presented by way of example only, and not limitation. Thus, the breadth and scope of the present disclosure should not be limited by any of the above-described exemplary embodiments. Moreover, any combination of the above-described elements in all possible variations thereof is encompassed by the disclosure unless otherwise indicated herein or otherwise clearly contradicted by context.

Additionally, while the processes described above and illustrated in the drawings are shown as a sequence of steps, this was done solely for the sake of illustration. Accordingly, it is contemplated that some steps may be added, some steps may be omitted, the order of the steps may be re-arranged, and some steps may be performed in parallel.

One or more embodiments are further described below.

Embodiments

A1. A cover for a lagoon, the cover comprising:
an expandable membrane;
a plurality of stretchable members coupled to the expandable membrane and configured to compress the expandable membrane; and
a plurality of restraining members coupled to the expandable membrane and configured to limit expansion of the expandable membrane.

A1a. The cover of embodiment A1, wherein the expandable membrane comprises a plurality of sections, and each of the plurality of stretchable members is at a location where two or more sections of the plurality of sections meet, and each of the plurality of restraining members is at a location where two or more sections of the plurality of sections meet.

A1b. The cover of embodiment A1a, wherein the plurality of sections forms a matrix.

A2. The cover of any one of embodiments A1, A1a, and A1b, further comprising a skirt surrounding the outer perimeter of the expandable membrane.

A3. The cover of embodiment A2, wherein the skirt comprises pressurized tubes.

A4. The cover of any one of embodiments A1-A3, further comprising a gas processing unit configured to process raw biogas from a gas outlet and to feed processed biogas into a gas inlet of the expandable membrane.

A5. The cover of any one of embodiments A1-A4, wherein the plurality of stretchable members comprise elastic material within the expandable membrane and connected to a top surface and a bottom surface of an interior of the expandable membrane.

A5'. The cover of any one of embodiments A1-A5, wherein the plurality of stretchable members comprise a spring and pulley.

A5". The cover of embodiment A5', wherein the spring comprises a clock spring.

A6. The cover of any one of embodiments A1-A5, A5', and A5", wherein a top surface of an exterior of the expandable membrane has a sloping contour.

A7. The cover of any one of embodiments A1-A5, A5', and A5", wherein a top surface of an exterior of the expandable membrane has a concave shape.

A8. The cover of any one of embodiments A6-A7, wherein an elasticity of the plurality of stretchable members is varied in order to define the top surface of the exterior of the expandable membrane.

A9. The cover of any one of embodiments A1-A8, wherein the plurality of stretchable members comprise elastic material within the expandable membrane and connected to a top surface and a bottom surface of an interior of the expandable membrane.

A10. The cover of any one of embodiments A1-A9, wherein the plurality of restraining members comprise rope within the expandable membrane and connected to a top surface and a bottom surface of an interior of the expandable membrane.

A11. The cover of embodiment A10, wherein the rope of each restraining member is configured to be loose when the expandable membrane is empty and configured to be taut when the expandable membrane is full.

A12. The cover of any one of embodiments A1-A11, further comprising a water collecting area and a water outlet for allowing water on a top surface of an exterior of the expandable membrane to escape.

A13. The cover of any one of embodiments A1-A12, wherein the expandable membrane comprises one or more of: an XR-5 geo-membrane, a Sattler Pro-Tex Polyplan composite, polypropylene, polyethylene, PEEK, PVC, PTFE, PPS, and ETFE.

A14. The cover of any one of embodiments A1-A13, wherein the expandable membrane is expandable in a vertical direction such that an outer perimeter of the expandable membrane is resistant to expansion.

B1. A system comprising:
a slurry lagoon; and
a cover for the slurry lagoon, the cover comprising:
an expandable membrane;
a plurality of stretchable members coupled to the expandable membrane and configured to compress the expandable membrane; and
a plurality of restraining members coupled to the expandable membrane and configured to limit expansion of the expandable membrane.

B1'. The system of embodiment B1, wherein the cover for the slurry lagoon is any one of embodiments A2-A14.

B2. The system of embodiment B1, further comprising a skirt surrounding the outer perimeter of the expandable membrane, wherein the skirt is within the slurry lagoon and configured to stay submerged in slurry in the slurry lagoon.

B2a. The system of embodiment B2, wherein the skirt is weighted so that it remains submerged within the slurry lagoon.

B3. The system of any one of embodiments B2 and B2a, wherein there is a gap between an edge of the slurry lagoon and the skirt, and a liquid within the gap seals the slurry lagoon to prevent gas leakage.

B4. The system of embodiments B1-B3, further comprising a water collecting area and a water outlet for allowing water on a top surface of an exterior of the expandable membrane to escape.

B5. The system of embodiment B4, further comprising piping coupled to the water outlet so that escaping water can pass through the pipe by gravity.

B6. The system of embodiment B4, further comprising a pump and piping coupled to the water outlet so that escaping water can pass through the pipe by pumping.

B7. The system of any one of embodiments B1-B6, further comprising a gas processing unit configured to process raw biogas from a gas outlet coupled to the slurry lagoon and to feed processed biogas into a gas inlet of the expandable membrane.

B8. The system of any one of embodiments B1-B7, further comprising one or more of: (i) a gas processing system, (ii) a mobile processing system, (iii) a thermal management system, (iv) a water collection and re-use system, and (v) an energy recovery system, each as disclosed in the "Anaerobic Digestion" section of this disclosure.

C1. A method for retrofitting an uncovered slurry lagoon with a cover, the method comprising:
installing a cover on an uncovered slurry lagoon,
wherein the cover is any one of embodiments A1-A14.

The invention claimed is:
1. A cover for a lagoon, the cover comprising:
an expandable membrane;
a plurality of stretchable members coupled to points on opposing sides within the expandable membrane and configured to compress the expandable membrane in a vertical direction; and
a plurality of restraining members coupled to points on opposing sides within the expandable membrane and configured to limit expansion of the expandable membrane in a vertical direction,
wherein the points on the opposing sides within the expandable membrane are on a top surface and a bottom surface of an interior of the expandable membrane.

2. The cover of claim 1, wherein the expandable membrane includes a gas inlet capable of allowing gas to flow into a space within the expandable membrane.

3. The cover of claim 1, wherein the expandable membrane comprises a plurality of sections, and each of the plurality of stretchable members is at a location where two or more sections of the plurality of sections meet.

4. The cover of claim 3, wherein each of the plurality of restraining members is at a location where two or more sections of the plurality of sections meet.

5. The cover of claim 3, wherein the plurality of sections forms a matrix.

6. The cover of claim 1, further comprising a skirt surrounding an outer perimeter of the expandable membrane.

7. The cover of claim 6, wherein the skirt comprises pressurized tubes.

8. The cover of claim 1, further comprising a gas processing unit configured to process raw biogas from a gas outlet and to feed processed biogas into a gas inlet of the expandable membrane.

9. The cover of claim 1, wherein the plurality of stretchable members comprise elastic material within the expandable membrane and are connected to the top surface and the bottom surface of the interior of the expandable membrane, or wherein the plurality of stretchable members comprise a spring and pulley.

10. The cover of claim 1, wherein a top surface of an exterior of the expandable membrane has a sloping contour, or wherein a top surface of an exterior of the expandable membrane has a concave shape, or wherein an elasticity of the plurality of stretchable members is varied in order to define the top surface of the exterior of the expandable membrane.

11. The cover of claim 1, wherein the plurality of restraining members comprise rope within the expandable membrane and are connected to the top surface and the bottom surface of the interior of the expandable membrane.

12. The cover of claim 11 wherein the rope of each restraining member is configured to be loose when the expandable membrane is empty and configured to be taut when the expandable membrane is full.

13. The cover of claim 1, further comprising a water collecting area and a water outlet for allowing water on a top surface of an exterior of the expandable membrane to escape.

14. A method for retrofitting an uncovered slurry lagoon with a cover, the method comprising:
installing a cover on an uncovered slurry lagoon,
wherein the cover is a cover according to claim 1.

15. The method of claim 14, wherein the cover has an average height h1 in an initial state, wherein the method further includes processing biogas from the slurry lagoon that passes through a gas processing system and releasing the processed biogas into the cover through an opening, such that processed biogas is stored within the cover and wherein after releasing the processed biogas into the cover, the cover has an average height h2 that is larger than h1.

16. A system comprising:
a slurry lagoon; and
a cover for the slurry lagoon, the cover comprising:
an expandable membrane;
a plurality of stretchable members coupled to points on opposing sides within the expandable membrane and configured to compress the expandable membrane in a vertical direction; and
a plurality of restraining members coupled to points on opposing sides within the expandable membrane and configured to limit expansion of the expandable membrane in a vertical direction,
wherein the points on the opposing sides within the expandable membrane are on a top surface and a bottom surface of an interior of the expandable membrane.

17. The system of claim 16, further comprising a skirt surrounding an outer perimeter of the expandable membrane, wherein the skirt is within the slurry lagoon and configured to stay submerged in slurry in the slurry lagoon.

18. The system of claim 17, wherein the skirt is weighted so that the skirt remains submerged within the slurry lagoon.

19. The system of claim 17, wherein there is a gap between an edge of the slurry lagoon and the skirt, and a liquid within the gap seals the slurry lagoon to prevent gas leakage.

20. The system of claim 16, further comprising a water collecting area and a water outlet for allowing water on a top surface of an exterior of the expandable membrane to escape.

21. The system of claim 20, further comprising piping coupled to the water outlet so that escaping water can pass through a pipe by gravity, or further comprising a pump and piping coupled to the water outlet so that escaping water can pass through the pipe by pumping.

22. The system of claim 16, further comprising a gas processing unit configured to process raw biogas from a gas outlet coupled to the slurry lagoon and to feed processed biogas into a gas inlet of the expandable membrane.

23. The system of claim 16, further comprising one or more of: (i) a gas processing system, (ii) a mobile processing system, (iii) a thermal management system, (iv) a water collection and re-use system, and (v) an energy recovery system.

* * * * *